(12) United States Patent
Li et al.

(10) Patent No.: US 9,073,995 B2
(45) Date of Patent: Jul. 7, 2015

(54) BLADDER CANCER TUMOR MARKER, ANTIBODY AND USE THEREOF

(75) Inventors: Chong Li, Beijing (CN); Zusen Fan, Beijing (CN); Honglian Zhang, Beijing (CN); Zhonghua Dai, Beijing (CN); Haidong Tang, Beijing (CN); Jun Chen, Beijing (CN)

(73) Assignee: Institute of Biophysics, Chinese Academy of Sciences, Beijing (CN)

( * ) Notice: Subject to any disclaimer, the term of this patent is extended or adjusted under 35 U.S.C. 154(b) by 149 days.

(21) Appl. No.: 13/814,446

(22) PCT Filed: Aug. 12, 2011

(86) PCT No.: PCT/CN2011/001345
§ 371 (c)(1),
(2), (4) Date: Feb. 26, 2013

(87) PCT Pub. No.: WO2012/019437
PCT Pub. Date: Feb. 16, 2012

(65) Prior Publication Data
US 2013/0164216 A1 Jun. 27, 2013

(30) Foreign Application Priority Data

Aug. 11, 2010 (CN) .......................... 2010 1 0251384

(51) Int. Cl.
| | | |
|---|---|---|
| G01N 33/53 | (2006.01) | |
| C07K 16/00 | (2006.01) | |
| C07K 16/28 | (2006.01) | |
| C07K 14/705 | (2006.01) | |
| G01N 33/574 | (2006.01) | |
| G01N 33/68 | (2006.01) | |
| C12N 15/113 | (2010.01) | |
| C12Q 1/48 | (2006.01) | |
| C12Q 1/02 | (2006.01) | |
| A61K 47/48 | (2006.01) | |
| A61K 51/10 | (2006.01) | |
| A61K 45/06 | (2006.01) | |
| A61K 39/395 | (2006.01) | |
| C07K 16/30 | (2006.01) | |
| C12N 9/10 | (2006.01) | |

(52) U.S. Cl.
CPC ......... C07K 16/2842 (2013.01); C07K 14/7055 (2013.01); G01N 33/57488 (2013.01); G01N 33/6854 (2013.01); C12N 15/1137 (2013.01); C12Q 1/48 (2013.01); C12Q 1/025 (2013.01); A61K 47/48607 (2013.01); A61K 51/1093 (2013.01); A61K 45/06 (2013.01); A61K 39/39558 (2013.01); C07K 16/3038 (2013.01); G01N 33/57484 (2013.01); G01N 2333/70546 (2013.01); G01N 2440/38 (2013.01); C07K 14/70546 (2013.01); C12N 9/1051 (2013.01); C12Y 204/01041 (2013.01)

(58) Field of Classification Search
None
See application file for complete search history.

(56) References Cited

U.S. PATENT DOCUMENTS

| | | | | |
|---|---|---|---|---|
| 4,281,061 | A | * | 7/1981 | Zuk et al. ........................ 435/7.9 |
| 4,761,406 | A | * | 8/1988 | Flora et al. ........................ 514/86 |
| 2008/0076137 | A1 | * | 3/2008 | Bovin et al. ..................... 435/7.5 |

FOREIGN PATENT DOCUMENTS

| | | |
|---|---|---|
| CN | 101052717 A | 10/2007 |
| CN | 101410532 A | 4/2009 |
| CN | 101638429 A | 2/2010 |
| CN | 101768214 A | 7/2010 |
| WO | 2004/018999 A2 | 3/2004 |
| WO | WO 2010/007213 A1 * | 1/2010 |
| WO | 2010/118374 A2 | 10/2010 |

OTHER PUBLICATIONS

Pochec' et al. Characterization of the oligosaccharide component of α3β1 integrin from human bladder carcinoma cell line T24 and its role in adhesion and migration. European Journal of Cell Biology 85 (2006) 47-57.*

Litynska et al. Profiling of integrin α3 β1 N-linked oligosaccharides using DNA-sequencer. International Symposium on Predictive Oncology and Intervention Strategies; Paris, France; Feb. 9-12, 2002; in the section on Molecular Pathology. p. 1.*

Zhao et al. N-Acetylglucosaminyltransferase III Antagonizes the Effect of N-Acetylglucosaminyltransferase V on α3β1 Integrin-mediated Cell Migration. The Journal of Biological Chemistry, 281, 32122-32130, 2006.*

Prokopishyn et al. Integrin α3β1 Expressed by Human Colon Cancer Cells is a Major Carrier of Oncodevelopmental Carbohydrate Epitopes. Journal of Cellular Biochemistry 72:189-209 (1999).*

Lityñska et al. Differences of α3β1 integrin glycans from different human bladder cell lines. Acta Biochimica Polonica 47(2):427-434, 2000.*

Galustian et al. L-selectin Interactions with Novel Mono- and Multisulfated Lewisx Sequences in Comparison with the Potent Ligand 3*-Sulfated Lewisa. J. Biol. Chem. 1999, 274:18213-18217.*

(Continued)

*Primary Examiner* — Maher Haddad
(74) *Attorney, Agent, or Firm* — Osha Liang LLP

(57) ABSTRACT

Provided in the present invention are an aberrantly glycosylated integrin, AG-α3β1, and use thereof as a bladder cancer marker. Also provided in the present invention are a hybridoma cell generating an anti-AG-α3β1 monoclonal antibody, a monoclonal antibody BCMab1 secreted by the same, and use of BCMab1 in the preparation of a medicament for the treatment of bladder cancer. Also provided in the present invention is use of inhibitors of GAL3ST2 and N-acetylgalactosaminyltransferase 1 in the preparation of a medicament for the treatment of bladder cancer.

8 Claims, 9 Drawing Sheets

(56) References Cited

OTHER PUBLICATIONS

Jamasbi et al. A Monoclonal Antibody to a Carbohydrate Epitope Expressed on Glycolipid and on α3β1 Integrin on Human Esophageal Carcinoma. Hybridoma and Hybridomics. 22(6):367-376, 2003.*

Takeuchi et al. IntercellUlar AdheSlon Induced by Anti-α3 IntegrIn (VLA-3) Antibodies. Experimental Cell Research 21 1, 133-141 (1994).*

International Search Report mailed on Nov. 24, 2011, by the State Intellectual Property Office of the People's Republic of China in corresponding International Application No. PCT/CN2011/001345, with English translation (10 pages).

Wang, Gang, "MicroRNA and bladder cancer"; Chinese Bulletin of Life Sciences, vol. 22, No. 3, Mar. 2010; pp. 262-266, Englishe abstract only.

Dyrskjot, Lars, et al., "Genomic Profiling of MicroRNAs in Bladder Cancer: miR-129 Is Associated with Poor Outcome and Promotes Cell Death in vitro"; Cancer Research, vol. 69, No. 11, Jun. 1, 2009; pp. 4851-4860.

Pochec, Ewa, et al., "Characterization of the oligosaccharide component of a3b1 integrin from human bladder carcinoma cell line T24 and its role in adhesion and migration"; European Journal of Cell Biology, vol. 85, (2006); pp. 47-57.

Shida, Kyoko, et al., "Unusual accumulation of sulfated glycosphingolipids in colon cancer cells"; Glycobiology, vol. 19, No. 9, Jun. 2009; pp. 1018-0133.

Hatanaka, Kenichi, et al., "Synthesis of a New Inhibitor of the UDP-GaINAc: Polypeptide Galactosaminyl Transferase"; Biochemical and Biophysical Research Communications, vol. 175, No. 2, Mar. 15, 1992; pp. 668-672.

Shi, Bi-Zhi, et al., "Gal3ST-2 involved in tumor metastasis process by regulation of adhesion ability to selectins and expression of integrins"; Biochemical and Biophysical Research Communications, vol. 332, (2005); pp. 934-940.

Tsubokawa, Daigo, et al., "A monoclonal antibody, PGM34, against 6-sulfated blood-group H type 2 antigen, on the carbohydrate moiety of mucin—Analysis of the epitope sequence and immunohistochemical study"; FEBS Journal, vol. 274, No. 7, (2007); pp. 1833-1848.

First Office Action and Search Report issued Jan. 17, 2013, by the State Intellectual Property Office of the People's Republic of China (SIPO), in corresponding Chinese Patent Application No. CN-2010102513846, with English translation [9 pages].

Gang, Luo, et al., "Expression and Clinical Significance of MUC1 and MUC11Y in Human Carcinoma of Bladder and Cystitis Glandularis"; Medical Journal of Wuhan University, vol. 26, No. 3, May, 2005 [6 pages], English abstract only.

Li, Gongchu, et al., "a3B1 integrin induced suppression of the Caco-2 epithelial cell IL-1 signaling pathway leading to NF-kB activation"; Cellular Immunology, vol. 231 (2004); pp. 30-39.

* cited by examiner

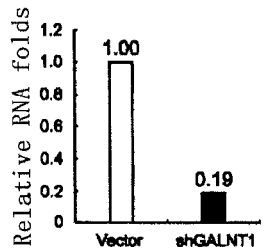 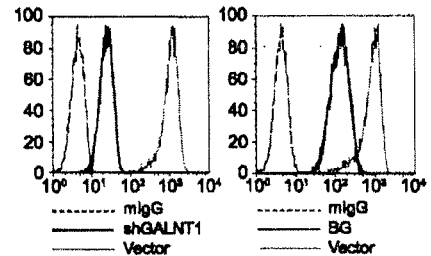
Fig. 8                Fig. 9
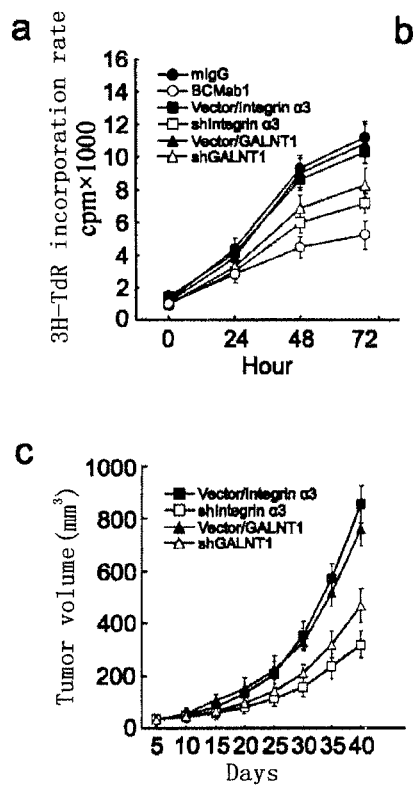 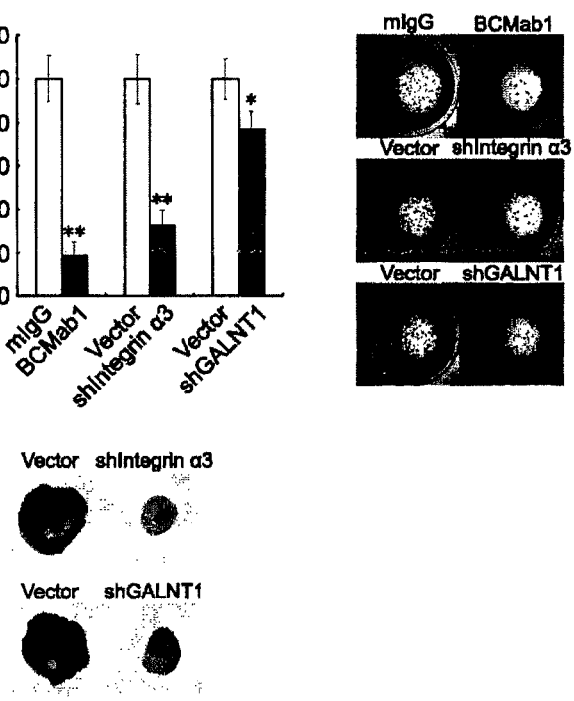
Fig. 10

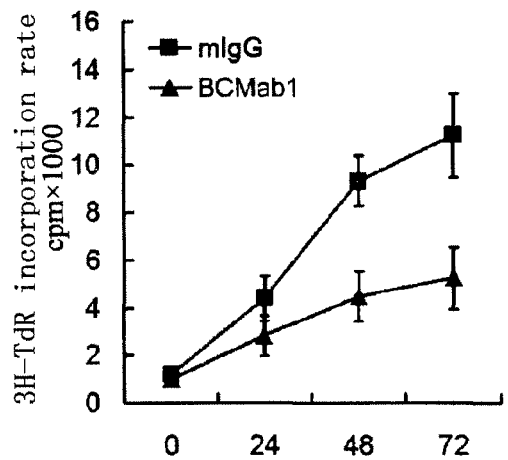

Fig. 12

Amino acid sequence of integrin α 3:
MGPGPSRAPRAPRLMLCALALMVAAGGCVVSAFNLDTRFLVVKEAGNPGSLFGYSVALHRQTERQQRYLLLAGAPRELAVPDGY
TNRTGAVYLCPLTAHKDDCERMNITVKNDPGHHIIEDMWLGVTVASQGPAGRVLVCAHRYTQVLWSGSEDQRRMVGKCYVRGND
LELDSSDDWQTYHNEMCNSNTDYLETGMCQLGTSGGFTQNTVYFGAPGAYNWKGNSYMIQRKEWDLSEYSYKDPEDQGNLYIGY
TMQVGSFILHPKNITIVTGAPRHRHMGAVFLLSQEAGGDLRRRQVLEGSQVGAYFGSAIALADLNNDGWQDLLVGAPYYFERKE
EVGGAIYVFMNQAGTSFPAHPSLLLHGPSGSAFGLSVASIGDINQDGFQDIAVGAPFEGLGKVYIYHSSSKGLLRQPQQVIHGE
KLGLPGLATFGYSLSGQMDVDENFYPDLLVGSLSDHIVLLRARPVINIVHKTLVPRPAVLDPALCTATSCVQVELCFAYNQSAG
NPNYRRNITLAYTLEADRDRRPPRLRFAGSESAVFHGFFSMPEMRCQKLELLLMDNLRDKLRPIIISMNYSLPLRMPDRPRLGL
RSLDAYPILNQAQALENHTEVQFQKECGPDNKCESNLQMRAAFVSEQQQKLSRLQYSRDVRKLLLSINVTNTRTSERSGEDAHE
ALLTLVVPPALLLSSVRPPGACQANETIFCELGNPFKRNQRMELLIAFEVIGVTLHTRDLQVQLQLSTSSHQDNLWPMILTLLV
DYTLQTSLSMVNHRLQSFFGGTVMGESGMKTVEDVGSPLKYEFQVGPMGEGLVGLGTLVLGLEWPYEVSNGKWLLYPTEITVHG
NGSWPCRPPGDLINPLNLTLSDPGDRPSSPQRRRRQLDPGGGQGPPPVTLAAAKKAKSETVLTCATGRAHCVWLECPIPDAPVV
TNVTVKARVWNSTFIEDYRDFDRVRVNGWATLFLRTSIPTINMENKTTWFSVDIDSELVEELPAEIELWLVLVAVGAGLLLLGL
IILLLWKCGFFKRARTRALYEAKRQKAEMKSQPSETERLTDDY

Fig. 13

Amino acid sequence of integrin β 1:
MNLQPIFWIGLISSVCCVFAQTDENRCLKANAKSCGECIQAGPNCGWCTNSTFLQEGMPTSARCDDLEALKKKGCPPDDIENPR
GSKDIKKNKNVTNRSKGTAEKLKPEDITQIQPQQLVLRLRSGEPQTFTLKFKRAEDYPIDLYYLMDLSYSMKDDLENVKSLGTD
LMNEMRRITSDFRIGFGSFVEKTVMPYISTTPAKLRNPCTSEQNCTSPFSYKNVLSLTNKGEVFNELVGKQRISGNLDSPEGGF
DAIMQVAVCGSLIGWRNVTRLLVFSTDAGFHFAGDGKLGGIVLPNDGQCHLENNMYTMSHYYDYPSIAHLVQKLSENNIQTIFA
VTEEFQPVYKELKNLIPKSAVGTLSANSSNVIQLIIDAYNSLSSEVILENGKLSEGVTISYKSYCKNGVNGTGENGRKCSNISI
GDEVQFEISITSNKCPKKDSDSFKIRPLGFTEEVEVILQYICECECQSEGIPESPKCHEGNGTFECGACRCNEGRVGRHCECST
DEVNSEDMDAYCRKENSSEICSNNGECVCGQCVCRKRDNTNEIYSGKFCECDNFNCDRSNGLICGGNGVCKCRVCECNPNYTGS
ACDCSLDTSTCEASNGQICNGRGICECGVCKCTDPKFQGQTCEMCQTCLGVCAEHKECVQCRAFNKGEKKDTCTQECSYFNITK
VESRDKLPQPVQPDPVSHCKEKDVDDCWFYFTYSVNGNNEVMVHVVENPECPTGPDIIPIVAGVVAGIVLIGLALLLIWKLLMI
IHDRREFAKFEKEKMNAKWDTGENPIYKSAVTTVVNPKYEGK

Fig. 14

BLADDER CANCER TUMOR MARKER, ANTIBODY AND USE THEREOF

CROSS REFERENCE TO RELATED APPLICATION

This is a national stage application of PCT/CN2011/001345, filed on Aug. 12, 2011, which claims priority of Chinese Patent Application No. CN 201010251384.6, filed on Aug. 11, 2010. This application claims the benefits and priority of these prior applications and incorporates the disclosures of these prior applications by reference in their entirety.

FIELD OF THE ART

The present invention belongs to a field of tumor immunology. Particularly, the present invention relates to a novel antigen AG-α3β1 and the preparation thereof (AG: Aberrant Glycosylation), and an anti-AG-α3β1 monoclonal antibody BCMab1. It is demonstrated at cytology and histology levels that AG-α3β1 is expressed on the membranes of human bladder tumor cells only, the antibody BCMab1 not only specifically recognizes AG-α3β1, but also effectively inhibits the proliferation of human bladder tumor cells at cellular level in vitro and in an animal model in vivo. The present invention also relates to a process for detecting bladder cancer in human using a competitive ELISA. In such a detecting process, the antigen in an immobile phase is human bladder cancer tumor marker AG-α3β1 according to the present invention, and the detection antibody is the antibody BCMab1 directed against human bladder cancer integrin α3β1.

BACKGROUND OF THE INVENTION

Bladder cancer is a tumor most commonly found in urinary systems. Although numerous steps were adopted for the treatment, 40-70% of the patients relapsed once or more than once and 10-15% of the patients developed more severe tumors or involved metastasis. Moreover, all these treating processes have apparent toxic and side-effects.

One important clinical task is to prevent relapse of bladder cancer after excision of tumors. Currently, the medicaments used for preventing relapse by bladder perfusion are mainly divided into the following several classes: (1) anti-tumor chemotherapeutic agents, such as Mitomycin C, etc.; (2) immunopotentiators, such as Bacillus Calmette-Guerin Vaccine (BCG), etc.; and (3) cytokines, such as interferon, etc. Although the above classes of medicaments, used either alone or in combination, achieved some effects in the reduction of the relapse rate after the operation of bladder cancer, the overall therapeutical effect is not desirable due to the presence of many issues such as low specificity, multiple drug resistance (MDR) of tumors, and so on. Moreover, because of their low molecular weights, the above classes of medicaments not only can act on the entire bladder and urethra unspecifically, but also can be absorbed by the mucous membranes of bladder and urethra, which easily results in topical or systematic toxic and side-effects. For instance, in the case of Mitomycin C and Bacillus Calmette-Guerin Vaccine which have more positive therapeutical effects, 90% of the patients who had received Bacillus Calmette-Guerin Vaccine were suffered from BCG cystitis and other side effects including hematuria, tetter, fever, arthritis, urethral stricture and the like, or infrequently, even some severe conditions, such as hepatitis, pneumonia, life-threatened septicemia and so on. Mitomycin C has fewer side effects, however still 5-25% of the patients who had received Mitomycin C were suffered from chemical cystitis and anaphylaxis, and other side effects included urethral stricture, marrow depression, calcification of bladder wall, and so on.

Integrin is a group of divalent cation-dependent cell surface receptors with a major function of mediating cell-matrix, cell-cell adhesion by binding to corresponding ligands, so as to further affect cell shapes, gene expression and regulation, cell proliferation and differentiation, apoptosis, and migration, infiltration and metastasis of tumor cells, etc. Integrin is composed of non-covalent subunits α and β. Various combinations result in different ligand-binding abilities. Integrin subunit α3 (CD49c) can be combined with subunit β1 (CD29) to form integrin α3β1. The ligands for integrin α3β1 are laminin (LN) and Collagen IV. In epithelial tissues, integrin α3β1 is mainly involved in the conglutination between cells and basilar membranes of epithelial cells and can adjust signal transduction, thereby impacting the biological features of cells. Integrin α3β1 is modified aberrantly on the surface of tumor cells, which is considered to cause a change in malignancy.

Anti-tumor targeted drugs are biological or chemical molecules (e.g. monoclonal antibodies) with an ability to recognize and kill tumor cells specifically. Bladder cancer is a tumor inside the body cavity of human, i.e. a "somatic test tube" of human body. Targeted drugs have high specificities with and strong lethal effects on target cells in vitro. Therefore, in terms of the treatment for bladder cancer, it is very important to find a novel targeted drug directed against bladder cancer in human.

In screening for bladder tumors, early detection and accurate prognosis of bladder cancer appear to be extremely critical for clinical treatment. For the past several years, the molecular markers, such as nuclear matrix protein, bladder tumor antigen and satellite instability etc. newly involved in clinic were also limited by their low sensitivities and specificities. Urine cytological analysis and cystoscopy are still the golden criteria for the diagnosis and monitoring of bladder cancer. Therefore, it is extremely necessary to find an effective and convenient process for diagnosing bladder cancer.

DISCLOSURE OF THE INVENTION

The inventors utilized human bladder cancer cell line T24 to immunize mice, so as to achieve hybridoma cells. ELISA was conducted to screen for antibody BCMab1 which can bind to T24 cells with a high specificity. It was demonstrated by immunohistochemistry and immunofluorescence that antibody BCMab1 showed a strong positive reactivity with bladder cancer cell line T24 and bladder cancer tissue of human, but no cross reactivity with normal bladder tissue or other non-bladder cancer cells.

In the present invention, the antigen recognized by antibody BCMab1 was captured by antibody BCMab1 using an immunoaffinity chromatography, and then identified as integrin α3β1 modified by aberrant glycosylation using a mass spectroscopy and carbohydrate chips. Such an antigen is designated as AG-α3β1, having an epitope in a carbohydrate structure shown as follow: [3OSO3]Galβ1-4(Fucα1-3)[6OSO3]GlcNAc. It has been demonstrated by the antibody BCMab1 that AG-α3β1 is only expressed on bladder tumor cells of human, and correlated positively with tumor staging and pathological grading of bladder cancer. AG-α3β1 can be used as a novel marker for bladder cancer tumors of human.

In the invention, T24 cells cultured in vitro and a nude mouse transplantation tumor model are treated with antibody BCMab1. It is found that antibody BCMab1 can effectively inhibit the proliferation of bladder cancer cell line T24. Antibody BCMab1 thus can be used as the targeted drug directed against bladder cancer of human.

In the invention, a diagnostic reagent is made from antibody BCMab1 and antigen AG-α3β1. Particularly, human bladder cancer tumor marker AG-α3β1, as an immobile phase, competes with a sample to be tested for antibody AbBC1, so as to detect bladder tumor cells in human urine.

It is also found in the invention that glycosyltransferase GALNT1 is highly expressed in bladder cancer and GALNT1-knockdown cells can down-regulate glycosylation level of integrin α3β1. Aberrant glycosylation of integrin α3 facilitates malignant transformation of bladder cancer. BCMab1 and immunotoxin BCMab1-Ra can significantly inhibit growth of the bladder cancer transplanted subcutaneously and orthotopically. BCMab1 treatment can recruit and activate natural killer (NK) cells surrounding bladder cancer. Both aberrant glycosylation of integrin α3β1 and severity of bladder cancer patients are associated with prognosis. As a result, aberrant glycosylation of integrin α3β1 can be considered as a new target for the diagnosis, prognosis and immunotherapy of bladder cancer.

Some creative ideas are brought up in the invention, including (1) preparing a mouse monoclonal antibody BCMab1 directed against human bladder cancer, which not only specifically binds to bladder cancer tissues of human, but also effectively inhibits proliferation of bladder cancer cell line T24 in vivo or in vitro; (2) revealing that the antigenic epitope AG-α3β1 recognized by such an antibody is a novel marker for human bladder cancer tumors, and demonstrating that such an epitope is only expressed on bladder tumor cells of human and correlated positively with tumor staging and pathological grading of bladder cancer; and (3) developing a highly sensitive competitive ELISA method for detecting human bladder cancer.

DETAILED DESCRIPTION OF THE INVENTION

The invention provides an aberrantly glycosylated integrin AG-α3β1, as well as a hybridoma cell generating a monoclonal antibody directed against such a tumor marker and the monoclonal antibody BCMab1 secreted by the same. The antigenic epitope recognized by the antibody BCMab1 is [3OSO3]Galβ1-4(Fucα1-3)[6OSO3]GlcNAc. Such a monoclonal antibody shows a strong positive reactivity with human bladder cancer cell line T24 and human bladder cancer tissues, but no cross reactivity with normal bladder tissue or other non-bladder cancer cells of human. In addition, the monoclonal antibody has a function of inhibiting proliferation of bladder cancer cell line T24 in cell cultures in vitro and in animal tumor models. The invention also provides an in vitro diagnostic kit comprising the monoclonal antibody BCMab1, and a process for detecting the content of the tumor marker in urine exfoliative cells using the monoclonal antibody BCMab1.

More specifically, one object of the invention is to provide an aberrantly glycosylated integrin AG-α3β1 characterized in that the integrin α3β1 has a carbohydrate structure: [3OSO3]Galβ1-4(Fucα1-3)[6OSO3]GlcNAc as an antigenic epitope. The carbohydrate structure [3OSO3]Galβ1-4 (Fucα1-3)[6OSO3]GlcNAc is represented by a structural formula shown as follow:

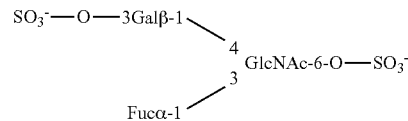

In a preferred embodiment of the invention, the integrin α3β1 has an α3 subunit having an amino acid sequence shown as SEQ ID No: 1 and a β1 subunit having an amino acid sequence shown as SEQ ID No: 2. Preferably, the aberrant glycosylation is located on the amino acid T (threonine) at position 740 of the α3 subunit.

Another object of the invention is to provide a binding molecule directed against the AG-α3β1 according to the invention. Such a binding molecule can specifically recognize or bind to the carbohydrate structure [3OSO3]Galβ1-4 (Fucα1-3)[6OSO3]GlcNAc as the antigenic epitope. Preferably, the binding molecule is a polyclonal antibody or monoclonal antibody. More preferably, the binding molecule is a monoclonal antibody.

In a preferred embodiment, the binding molecule is an anti-AG-α3β1 monoclonal antibody BCMab1, and the monoclonal antibody is secreted by the hybridoma cell line deposited as CGMCC No. 3845.

Another object of the invention is to provide a conjugate, wherein the binding molecule of the invention is conjugated with a substance selected from the group consisting of a biological marker, an antitumor drug, a toxin and a radioactive agent. Preferably, the conjugate is an immunotoxin BCMab1-Ra prepared from BCMab1 and ricin A chain connected by a heterogeneous difunctional crosslinker such as SPDP (N-succinimidyl 3-(2-pyridyldithio) propionate), MBS (m-Maleimidobenzoyl-N-hydroxysuccinimide ester), or 2-IT (2-Iminothiolane), etc. The connection method between an antibody and ricin A chain is well known and can be found in the following references for details: Shen, B. Connection between monoclonal antibody and toxin, *Monoclonal Antibody Communication* 1989; 2: 51; Cumber A J, et al. Preparation of antibodytoxin conjugates, *Methods Enzymol* 1985; 112:207; and Cros o, et al. Biochemical aspect of immunotoxin preparation, *J. Immunol. Meth.* 1985; 81:283.

Another object of the invention is to provide a pharmaceutical composition which comprises an effective dose of the binding molecule according to claims 3 or 4 or the conjugate according to claim 5, and a pharmaceutically acceptable carrier, diluents or excipient.

A further object of the invention is to provide a kit for detecting bladder cancer, which comprises the binding molecule of the invention, the conjugate of the invention, or AG-α3β1; and optionally another reagent for detecting bladder cancer. In a preferred embodiment, the detection is carried out by an enzyme linked immunosorbent assay. Preferably, the enzyme linked immunosorbent assay is a competitive enzyme linked immunosorbent assay, wherein AG-α3β1 of the invention, as an immobile phase, competes with a sample to be tested for the antibody of the invention.

In a preferred embodiment, the sample to be tested in said kit is urine or bladder tissue.

Another object of the invention is to provide a hybridoma cell line secreting the antibody BCMab1 directed against integrin α3β1 of human bladder cancer, which is deposited as CGMCC No. 3845.

A further object of the invention is to provide use of the pharmaceutical composition of the invention in preparation of the medicament for the treatment of bladder cancer. In a preferred embodiment, the medicament is used in a combination therapy with other drugs for the treatment of bladder cancer. Said other drugs for the treatment of bladder cancer are preferably selected from the group consisting of antitumor chemotherapeutic agent, immunoreinforcing agent, and cytokines; and more preferably a group consisting of thiotepa (TSPAP), Mitomycin C (MMC), Bacillus Calmette-Guerin Vaccine (BCG), cisplatin (DDP), adriamycin (ADM) and interferon. Further more preferably, said medicament and said other drugs for the treatment of bladder cancer are used simultaneously, separately or sequentially for the treatment of human or animal bodies. Still preferably, said medicament and said other drugs for the treatment of bladder cancer, formulated in a same or different preparations, are co-administered to the subjects in need thereof through a same or different routes.

Another object of the invention is to provide use of the AG-α3β1 or antibody of the invention, optionally combined with other indicators for the diagnosis or prognosis of bladder cancer, in the diagnosis and/or prognosis of bladder cancer.

Another object of the invention is to provide use of the AG-α3β1 of the invention for preparing and screening antibodies, wherein the AG-α3β1 is used as an immunogen to immunize animals, so as to obtain monoclonal or polyclonal antibodies, or the AG-α3β1 is used as an antigen to screen and prepare antibodies by a phage, yeast or ribosome display technique. Another object of the invention is to provide use of an RNAi sequence directed against GAL3ST2 in preparation of the medicament for the treatment of bladder cancer. Preferably, the nucleotide sequence of the RNAi is shown as SEQ ID No: 3.

Another object of the invention is to provide use of an inhibitor of N-acetylgalactosaminyltransferase 1 in preparation of the medicament for the treatment of bladder cancer. Preferably, the inhibitor includes the nucleotide sequence of the RNAi as shown by SEQ ID No: 4, uridine 5'-phosphoric (1-hexadecanesulfonic) anhydride, and Ammonium (3-Acetamido-2,6-anhydro-3-deoxy-D-glycero-L-gluco-heptitol-1-yl) (Uridine-5'-yl)Diphosphate.

Another object of the invention is to provide a process of screening for a potential substance to treat bladder cancer, which comprises the steps of:

(1) treating a system expressing N-acetylgalactosaminyltransferase 1 protein or GAL3 ST2 protein with a candidate; and (2) detecting the expression or activity of the N-acetylgalactosaminyltransferase 1 protein or GAL3ST2 protein in the system;

wherein, if the candidate can reduce the expression or activity of the N-acetylgalactosaminyltransferase 1 protein or GAL3ST2 protein, then the candidate is indicated to be a potential substance to treat bladder cancer.

Yet another object of the invention is to provide use of N-acetylgalactosaminyltransferase 1 in the diagnosis and/or prognosis of bladder cancer.

DESCRIPTION OF THE FIGURES

In FIG. 2, bladder cancer cells T24 were treated with iodic acid to destroy the carbohydrate antigen structure, so that antibody BCMab1 cannot recognize and no positive reaction with a brown color was present. Anti-MUC1 antibody (commercially purchased from Novocastra Laboratories Ltd, UK) is an antibody known to bind to carbohydrate structures only, which was used as a control herein. Anti-CK20 antibody (Novocastra Laboratories Ltd, UK) is an antibody known to bind to proteinic polypeptides only, which was also used as a control herein;

FIG. 8. Quantitative RT-PCR detection for GALNT1 silence effect in EJ cells;

FIG. 9. GALNT1 silence almost blocked BCMab1 staining. T24 cells and an inhibitor for GALNT1, i.e. BG were co-incubated for 7 days, and then stained with BCMab1;

FIG. 10. Knockdown of integrin α3 or GALNT1 inhibited cancer cell proliferation and tumor growth. (a) Silence of integrin α3 or GALNT1 inhibited proliferation of T24 cells. Integrin α3- or GALNT1-knockdown T24 cells or BCMab1 (10 μg/ml)-treated T24 cells, after cultured for 24-72 hours, were detected for cell proliferation by $^3$H-TdR incorporation assay. (b) Integrin α3- or GALNT1-silenced cell lines could not grow in a soft agar. After a treatment with BCMab1 (10 μg/ml), the growth of T24 cells was also inhibited in a soft agar. (c) Silence of integrin α3 or GALNT1 inhibited growth of bladder cancer. T24 cells transfected with integrin α3 or GALNT1 were injected subcutaneously into back of a BALB/c mouse. The tumor sizes were measured periodically, and averaged (the left panel). The right panel shows the tumor tissues;

FIG. 12. Antibody BCMab1 inhibited the proliferation of tumor cells;

FIG. 13. Amino acid sequence of integrin α3 subunit (SEQ ID NO: 1);

FIG. 14. Amino acid sequence of integrin β1 subunit (SEQ ID NO: 2);

DETAILED EMBODIMENTS OF THE INVENTION

Figure 1:
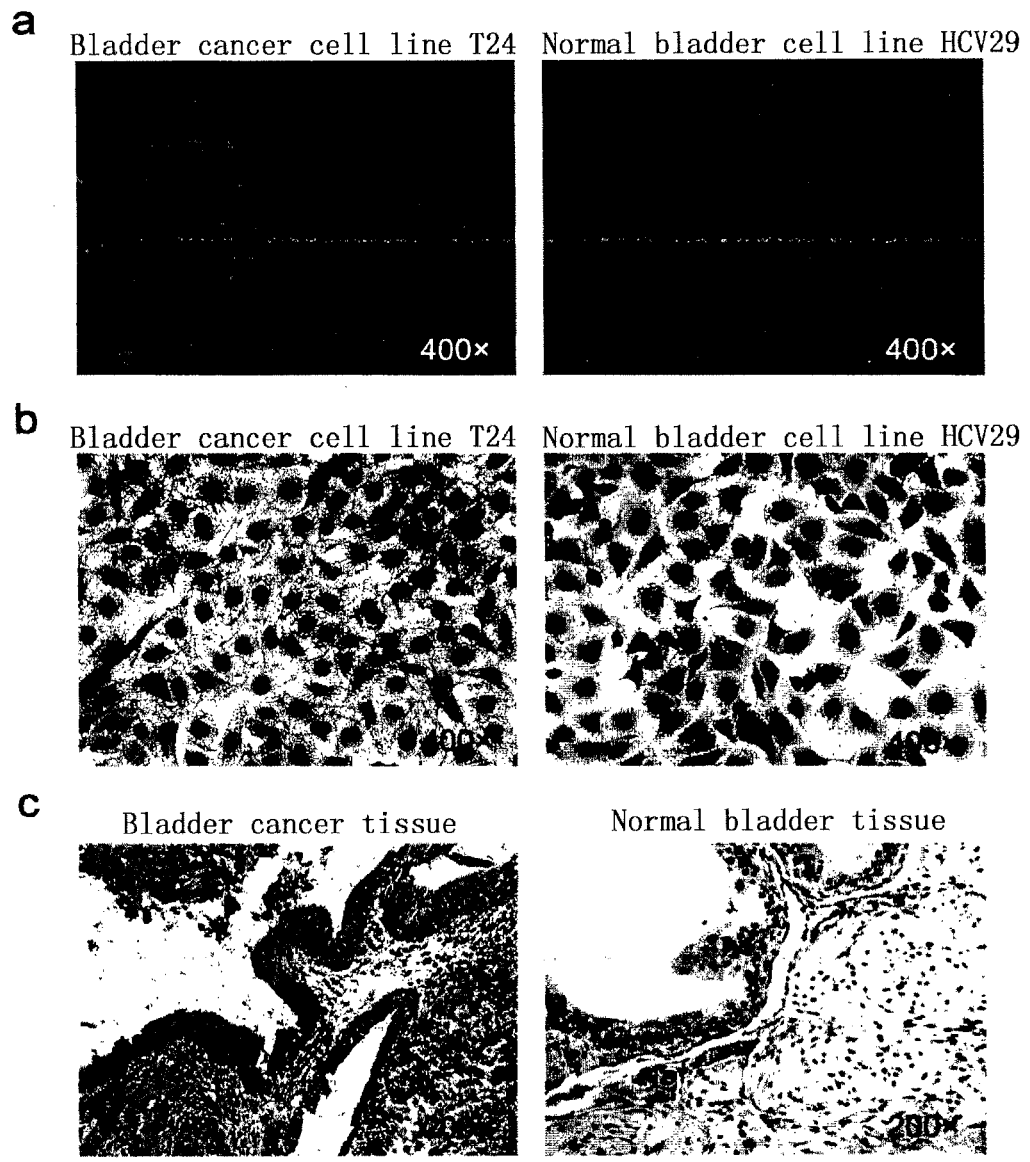
FIG. 1. BCMab1 specifically recognized bladder cancer cell line and bladder cancer tissue. (a, b) It was shown by immunofluorescence and immunohistochemisty that BCMab1 stain was positive for bladder cancer cell line T24 cells and negative for normal bladder cancer cell line HCV29. (c) BCMab1 stain was positive for bladder cancer tissues and negative for normal bladder mucosal tissues (IHC)

As used herein, the term "binding molecules" means intact immunoglobulins, including monoclonal antibodies and polyclonal antibodies, such as chimeric antibodies, humanized antibodies or human monoclonal antibodies, or antigen binding fragments which can bind to antigenic epitopes, including Fab, F(ab'), F(ab')2, Fv, dAb, Fd, complementary determining region (CDR) fragment, single-chain antibodies (scFv), bivalent single-chain antibodies, single-chain phage antibodies, bispecific double-chain antibodies (diabodies), triabodies, tetrabodies, and proteins or polypeptides binding to antigenic epitopes, etc. The above fragments can be generated through synthesis, enzymatic or chemical lysis of intact immunoglobulins, or recombinant DNA technology-genetic engineering. All these preparation methods are well known in the art, for example, E. Harlow and D, Lane (1988) ed. Antibodies: A Laboratory Manual, Cold Spring Harbor Laboratory, Cold Spring Harbor, N.Y., which is incorporated herein by reference.

As used herein, the term "binding molecules" include all classes and subclasses of immunoglobulins known in the art. According to the amino acid sequences of their heavy-chain constant domains, binding molecules can be divided into 5 major classes of intact antibodies: IgA, IgD, IgE, IgG and IgM, wherein some classes can be further divided into subclasses (isotypes), e.g. IgA1, IgA2, IgG1, IgG2, IgG3 and IgG4.

An anti-AG-α3β1 monoclonal antibody, BCMab1 is provided in the invention, and anti-AG-α3β1 polyclonal antibodies and other monoclonal antibodies can be easily generated by a person skilled in the art. The general processes for preparing a monoclonal antibody from hybridoma are well known. The cell lines that generate immortal antibodies can be prepared through cell fusion and other techniques, such as transformation of B lymphocytes by oncogenic DNA, or EB (Epstein-Barr virus) transfection.

Physical selection is one example of the conventional processes for obtaining all human antibodies, and includes but is not limited to screening by a phage, yeast or ribosome display technique. The detailed procedure comprises a step of selecting a ligand (antibody) binding to the target protein (antigen) accordingly. There are two conventional physical selection methods. In the first method, an antigen is fixed on a solid support and incubated with an antibody library; after recognition and binding between the antibodies and antigens, unbound antibodies are rinsed off, and the antibodies bound specifically are eluted, collected, identified and stored. In the second method, an antigen is labeled (with biotin or fluorescence, usually) and then the antibodies specifically binding to such an antigen are screened out. In phage, bacterium and yeast display techniques, a living organism is used for the amplification and display, and phenotype and genotype are combined; whereas ribosome and puromycin mRNA display techniques rely on PCR amplification, in vitro RNA translation for obtaining a ligand, and then the binding to corresponding cDNA via a noncovalent bond or a covalent bond. These methods usually require several rounds of screenings. Since the antigenic specificities are known in advance, therefore the specificities of the resultant antibodies are definite. All these methods are well known by a person skilled in the art, and described detailedly in Antibody Engineering Drugs (Zhen, Y. and Shao, R., Chemical Industry Press, published on 2002 Nov. 1).

The invention first reveals a relation between the increase of AG-α3β1 and development/prognosis of bladder cancer, and demonstrates that AG-α3β1 can be used for the diagnosis, therapeutic direction and prognosis. It is understood by a person skilled in the art that all kinds of methods, including but not limited to immunohistochemistry, immunoenzyme technique, enzyme linked immunosorbent assay, immunofluorescence technique, radioimmunoassay, immune-colloidal gold labeling technique and so on, can be applied to detect AG-α3β1.

After determination of the coating antibody and detection antibody used in the kit of the invention, all types of markers, which can be detected commonly by binding to the detection antibodies in the field, can be applied. The markers applied in the invention are not specifically limited, as long as they can bind to the detection antibodies and, after treated properly, accurately indicates whether AG-α3β1 is present in the samples to be detected and the existing amount thereof. For instance, the markers can be selected from (but not limited to): horseradish peroxidase, alkaline phosphatase, glucose oxidase, β-D-galactosidase, urease, catalase, or glucoamylase.

Where some of the above enzymic markers are used, some substances that bind to the corresponding enzymes are also required, so that the existing status or amounts of the markers can be reported by color development and so on. The substances include (but are not limited to): o-phenylene diamine (OPD), tetramethyl benzidine (TMB) and ABTS for horseradish peroxidase; and p-nitrophenyl phosphate (p-NPP) for alkaline phosphatase.

In order to eliminate false positive and false negative, a quality control (i.e. control) is intended to be set up during the detection. In one example of the invention, the quality control is prepared by diluting a standard AG-α3β1 preparation and serum obtained from healthy volunteers. In addition, if quantitative results are desired, a person skilled in the art understands that several standard AG-α3β1 preparations with known concentrations can be set up during the detection. The standard preparations can be set up by conventional methods.

As used herein, the "sample" means a substance extracted from human or animal bodies, and includes but is not limited to: urine, plasma, serum, bladder tissue, and other tissues or extraction liquids thereof. Preferably, the "sample" is urine. After lysis, bladder cancer cells release various types of soluble molecules, including AG-α3β1.

Pharmaceutical Composition and Use Thereof

The invention further provides a pharmaceutical composition, which comprises:
(a) an effective amount of the binding molecules of the invention; and a pharmaceutically acceptable carrier, diluents or excipient.

As used herein, the term "the composition of the invention" includes pharmaceutical compositions, as long as they comprise the binding molecules of the invention as an active component.

In the invention, the term "comprise" means that all types of components can be applied to the mixture or composition of the invention.

In the invention, a "pharmaceutically acceptable" component is a substance which is suitably used in human and/or animals without causing excessive adverse side effect (such as toxicity, irritation and allergy), i.e. a substance with a reasonable efficiency/risk ratio. As used herein, the term "an effective amount" means the amount of a therapeutical agent to treat, alleviate or prevent diseases or conditions, or the amount showing detectable therapeutical or prophylactic effect. The accurate effective amount for a particular subject depends on its somatotype and healthy condition, feature and severity of the disease, as well as the selected therapeutical agents and/or the combination thereof for administration. As a result, predetermination of the accurate effective amount is meaningless. However, in terms of some specified circumstances, the effective amount can be determined by a clinical physician through conventional experiments. For the purpose of the invention, the effective amount means administration of 0.01 μg/kg-500 μg/kg, preferably 0.05 μg/kg-200 μg/kg body weight of the active substance of the invention into individuals.

The pharmaceutical composition can further comprise a pharmaceutically acceptable carrier. The term "a pharmaceutically acceptable carrier" means a carrier used for administering a therapeutical agent. A pharmaceutically acceptable carrier satisfies the following criteria: it neither induces generation of the antibodies which harm the individuals who have received the composition, nor causes excessive toxicity upon administration. Such carriers are well known by a person skilled in the art. A sufficient discussion of the pharmaceutically acceptable carriers can be found in Remington's Pharmaceutical Sciences, Mack Pub. Co., N.J. 1991. Solid carriers include but are not limited to: starch, lactose, dicalcium phosphate, microcrystalline cellulose, sucrose and kaolin; and liquid carriers include but are not limited to: saline, buffer, glucose, water, glycerol, ethanol, adjuvant, polyethylene glycol, nonionic surfactant and edible oil (such as corn oil, peanut oil and sesame oil), as long as they are suitable for the properties of the active components and the desired specific administration routes. The adjuvants commonly used for preparing pharmaceutical compositions can also be included advantageously, for example, a flavoring agent, pigment, preservative and antioxidant such as vitamin E, vitamin C, BHT and BHA. Additionally, these carriers possibly further comprise auxiliaries such as a wetting agent or emulsifying agent, pH buffer substance and so on.

The pharmaceutical composition of the invention can be prepared into any conventional preparation forms by conventional methods.

The dosage forms of the pharmaceutical composition according to the invention are various, as long as they enable the active component to enter into mammalian bodies effectively. The composition can be formulated into any forms suitable for the desired administration routes. For instance, the pharmaceutical composition can be made into tablets, pills, powder, lozenges, pouches, cachets, elixirs, suspensions, emulsions, solutions, syrups, aerosol (as a solid or in a liquid matrix), ointment, soft and hard gel capsules, suppositories, aseptic injections, aseptic packagings of powder, and so on.

The binding molecules or their pharmaceutically acceptable derivatives, modifications, and combinations thereof can be administered through bladder infusion, intravenous, intramuscular or subcutaneous injection, and an oral route, etc., preferably through bladder infusion. The composition of the invention and the pharmaceutical composition thereof can also be stored in a disinfector suitable for injection or dripping.

The composition of the invention, once prepared, can be given to a subject directly. The subjects to be prevented or treated can be animals; particularly human. The therapeutical dose regimen can be a single-dose regimen or a multidose regimen, which can be adjusted for providing an optimal therapeutical response. For example, due to the stringent requirements of the therapeutical status, several separated doses can be given every day, or the dose can be reduced proportionally.

The composition or medicament of the invention can further comprise other active components, e.g. other drugs for the treatment of bladder cancer used in a combination therapy. Said other drugs for the treatment of bladder cancer are selected from preferably the group consisting of antitumor chemotherapeutic agent, immunoreinforcing agent, and cytokines; and more preferably a group consisting of thiotepa (TSPAP), Mitomycin C (MMC), Bacillus Calmette-Guerin Vaccine (BCG), cisplatin (DDP), adriamycin (ADM) and interferon. Where two or more drugs mentioned above are administered in a combination, normally an effect that excels those caused by administering the two drugs separately is achieved. Preferably, the drugs or other preparations administered in a combination do not interfere with the therapeutical activity of the binding molecules according to the invention.

It was found in the invention that knockout of N-acetylgalactosaminyltransferase 1 (GalNAc-T1) expression could inhibit the proliferation of bladder cancer cells and the growth of tumors. Thus a person skilled in the art understands that all inhibitors for GALNT1 can be applied to prepare the drugs for the treatment of bladder cancer. The inhibitors include but are not limited to the nucleotide sequence (SEQ ID No: 4) of RNAi mentioned in Examples, an inhibitor for GALNT1, i.e. ammonium (3-Acetamido-2,6-anhydro-3-deoxy-D-glycero-L-gluco-heptitol-1-yl) (Uridine-5'-yl)Diphosphate disclosed by Thiem J. (see the following references: J Org. Chem. 2000 Jan. 14; 65(1):24-9. Synthesis of novel donor mimetics of UDP-Gal, UDP-GlcNAc, and UDP-GalNAc as potential transferase inhibitors.), uridine 5'-phosphoric (1-hexadecanesulfonic) anhydride disclosed by Elbein A D (see the following reference: Biochem Biophys Res Commun. 1991 Mar. 15; 175(2):668-72. Synthesis of a new inhibitor of the UDP-GalNAc: polypeptide galactosaminyl transferase.), a inhibitor for GalNAc-T1 disclosed in WO 2010/118347 A2, and the like.

It was also found in the invention that GALNT1 mRNA expression level was higher in bladder cancer tumor tissues than in normal tissues. Therefore, GALNT1 mRNA can be used as indicator for diagnosis and/or prognosis of bladder cancer. Conventional methods for detecting GALNT1 mRNA are known by a person skilled in the art. Specifically, the tissue to be detected and the normal control tissue are obtained, and detected for their GALNT1 mRNA contents; if the GALNT1 mRNA level is higher in the tissue to be detected than in the normal control tissue by 2 folds or more, then the tissue to be detected is indicated to be a bladder cancer tissue.

It was further found in the invention that knockout of GAL3ST2 (galactose: 3-O-sulfonyltransferase 2) expression inhibited the proliferation of bladder cancer cells and the growth of tumors. Thus a person skilled in the art understands that all inhibitors for GAL3ST2 can be applied to prepare the drugs for the treatment of bladder cancer. The inhibitors include but are not limited to the nucleotide sequence (SEQ ID No: 3) of RNAi mentioned in Examples and an RNAi inhibitor for GAL3ST2, i.e. 5'atgtggttcgacttcggct3' disclosed by Xing-Zhong Wu (Biochemical and Biophysical Research Communications 332 (2005) 934-940), etc.

The invention is further set forth by incorporating the detailed Examples. It will be understood that these Examples are only intended to illustrate the invention, rather than restrict the scope of the invention. In the following Examples, the experiments without specified conditions were conducted in accordance with conventional conditions, such as the conditions defined in Sambrook, et al, Molecular Cloning: A Laboratory Guideline. (New York: Cold Spring Harbor Laboratory Press, 1989) or the conditions recommended by the manufacturers. Unless indicated otherwise, percentages and parts were calculated by weight. Unless defined otherwise, all professional terms and scientific phrases used herein have the same meanings as those well known by a person skilled in the art. In addition, any methods and materials similar with or equivalent to the contents recited herein can be applied in the invention. The preferred methods or materials described herein are intended for exemplification only.

EXAMPLE 1

Preparation and Purification of BCMab1 Monoclonal Antibody (1) Preparation of Hybridoma Balb/C mice (commercially purchased from Vital River Laboratory Animal Technology Co. Ltd., Beijing) were immunized with human bladder cancer cell line T24 (ATCC: HTB-4) by intraperitoneally injecting a dose of $1 \times 10^7$ cells/ml PBS. After two weeks, the mice were immunized again with the same injection volume and method. While the serum titer of the mice met the requirement, cell fusion was arranged. The mice were boosted three days before the fusion. At the same time, mouse myeloma cells Sp2/0 (ATCC CRL-1772) were prepared.

The sensitized B lymphocytes were fused with the myeloma cells (Practical Immunology, Yang, Y. ed., Changchun Press, published in December, 1994), and selectively cultured (using peritoneal macrophages of the mice as feeder cells) in HAT medium (purchased from Invitrogen Co.; HAT is an enumerate of the initials of hypoxantin, aminopterin and thymidin; HAT medium is thus a cell culture medium containing these three substances).

Next, the supernatant of the hybridoma cell culture was detected by ELISA. More specifically, T24 cells ($1\times10^5$ cells/ml) were coated onto a 96-well plate, 100 μl/well, and cultured at 37° C. overnight. After cell adherence, 4% paraformaldehyde was added, and the plate was fixed at room temperature for 10 min, then washed for 3 times. Subsequently, 100 μl of the supernatant to be detected was added and incubated at 37° C. for 1 hour. Following 3 times of washing, an enzyme-labeled secondary antibody (anti-mouse IgG-HRP) (commercially purchased from Zhongshanjinqiao Biological technology Co. Ltd., Beijing) was added and incubated at 37° C. for 1 hour. Following another 3 times of washing, 50 μl TMB (commercially purchased from Zhongshanjinqiao Biological technology Co. Ltd., Beijing) was added for color development, and kept at room temperature for 5 min. Then 50 μl stop buffer was added. In the end, the OD values were measured at a wavelength of 450 nm by a microplate reader. An OD value which is higher than that of the negative control by 2 folds or more is considered as a positive result.

Then, the selected positive hybridoma cells were clonally cultured (through a limiting dilution, and using peritoneal macrophages of the mice as feeder cells). Following 2-3 rounds of clonal cultures, stable hybridoma cell clones that could generate high-titer monoclonal antibodies were obtained. The hybridoma cell clones were then amplified, cultured, frozen and stored.

One type of the positive hybridoma cells in the invention is the hybridoma cell line secreting monoclonal antibodies directed against human bladder cancer. This hybridoma cell line was deposited in China General Microbiological Culture Collection (CGMCC, Beijing, China), with an accession number CGMCC No. 3845, on May 21, 2010.

(2) Preparation and Purification of Monoclonal Antibody BCMab1

The above hybridoma cells which secrete BCMab1 were inoculated into the abdominal cavities of Balb/C mice, so as to prepare ascites; then the monoclonal antibodies were extracted from the ascites. The monoclonal antibody BCMab1 was purified using Protein G affinity chromatography. First, a Protein G affinity chromatographic column (purchased from "GE" Co.) was prepared, and then balanced with PBS (Phosphate Buffered Saline). The ascites containing monoclonal antibody BCMab1 was passed through the column, then the column was washed with PBS till its OD value approached zero. The column was then eluted with a 0.2 M glycine-HCl solution (pH 2.8), and the eluent was collected. After the OD value of each collecting tube was measured, the eluent with the OD value within the peak range was retained, concentrated by dialysis, then frozen and stored at 20° C.

EXAMPLE 2

Identification of Monoclonal Antibody BCMab1

Normal bladder tissue cells HCV29 were purchased from Peking University Health Science Center. Cell lines T24, EJ, HepG2, LoVo, 293, A375, Jurkat, PC-1, MCF-7, K562, Hela, and other cell lines were purchased from ATCC (Rockville, Md., US). Bladder cancer tissues and normal tissues of human were received from The Second Affiliated Hospital of Kunming Medical University, with informed consents. BALB/C mice and nude mice were both purchased from Chinese Academy of Medical Science Institute of laboratory animal.

Bladder cancer tissue slices of human (received from Peking University Third Hospital) were stained immunohistochemically with the monoclonal antibody BCMab1 prepared in Example 1 using a conventional method. The result, as shown in FIG. 1, indicated that the bladder cancer tissues of human showed positive reactivity after stained with the monoclonal antibody BCMab1, a secondary antibody (anti-mouse IgG-HRP) and DAB substrate (Zhongshanjinqiao Biological technology Co. Ltd., Beijing); whereas the normal tissues of human showed negative reactivity after being stained with the monoclonal antibody BCMab1, a secondary antibody and substrate.

Bladder cancer cells T24 and other cells were detected by the monoclonal antibody BCMab1 using a flow cytometer, and normal human tissues were assayed immunohistochemically. The results, as shown in Table 1 and FIG. 1, indicated that the monoclonal antibody BCMab1 showed a strong positive reactivity with T24 and EJ cells (ATCC CRL-1888), but no cross reactivity with other non-bladder cancer cells or normal tissues of human. Particularly, BCMab was able to stain human bladder cancer cell lines EJ and T24, rather than nonmalignant uretal epithelial cell line HCV29 and systematic tumor cells (FIG. 1a, 1b and Table 1). In order to investigate the specificity of BCMab1 to bladder cancer, 123 tumor tissues and 56 normal tissues were screened immunohistochemically. The results indicated that BCMab1 stained bladder cancer tissues only, and showed negative staining for normal bladder tissues and other tissues, such as liver, brain, adrenal gland, pancreas, stomach, colon, breast, lung, ovary, cardiac muscle, thyroid gland, lymph node and marrow (FIG. 1c, Table 1, unshown data). As a result, BCMab1 can specifically recognize the antigen on membranes of bladder cancer cells.

TABLE 1

Detection of immune responses of monoclonal antibody BCMab1 directed against human bladder cancer to various cells and tissues by flow cytometry and immunohistochemisty

| Cell line | BCMab1 | Normal tissue | BCMab1 |
| --- | --- | --- | --- |
| Human bladder cancer cell line EJ | + | Liver | − |
| Human bladder cancer cell line T24 | + | Brain | − |
| Normal human uretal epithelial cell line HCV29 | − | Adrenal gland | − |
| Human hepatic cancer cell line HepG2 | − | Pancreas | − |
| Human colon cancer LoVo | − | Stomach | − |
| Human malignant melanoma cell line A-375 | − | Colon | − |
| Human embryonic kidney cell line 293 | − | Breast | − |
| Human T cell tumor Jurkat | − | Lung | − |
| Human prostate cancer cell line PC-1 | − | Ovary | − |
| Human breast cancer cell line MCF-7 | − | Cardiac muscle | − |
| Human cervical cancer cell line HeLa | − | Thyroid gland | − |
| Human chronic leukemia cell line K562 | − | Lymph node | − |
| Human normal peripheral blood monouclear cell | − | Marrow | − |

EXAMPLE 3

Identification and Preparation of Antigen AG-α3β1

Human bladder cancer cell line T24 was cultured in a RPMI-1640 medium containing 10% fetal bovine serum (purchased from Invitrogen Co.). After digested with 0.25% pancreatin, $1\times10^8$ T24 cells were washed with PBS for 3 times. Then 100 μg monoclonal antibody BCMab1 was added, incubated at 4° C. for 2 hours, and washed with PBS for 3 times. The cells were lysed with 1 ml detergent lysis buffer (50 mM Tris-HCl, pH 8.0; 150 mM NaCl; 0.02% sodium azide; 0.1% SDS; 100 μg/ml PMSF; 1 μg/ml Aprotinin; 1% NP-40; 0.5% sodium deoxycholate) for 30 min, and centrifuged at 12,000 g for 10 min. The supernatant was separated and passed through the Protein G affinity chromatographic column. The column was washed with PBS till its OD value approached zero. Subsequently, elution was carried out using a 0.2 M glycine-HCl solution (pH 2.8), and the eluent was collected. The OD value of each collecting tube was measured, and then the eluent with an OD value within the peak range was retained, and identified to be human integrin α3β1 by mass chromatographic analysis (see Table 2).

Mass spectrometry: protein gel was cut into small pieces. Pierce Silver Staining Kit and mass chromatographic analysis (Pierce, US) were utilized. Mass chromatographic analysis was conducted for the tryptic peptide generated from digestion of the gel (NanoLC-LTQ, Thermo Finnigan).

Figure 2:
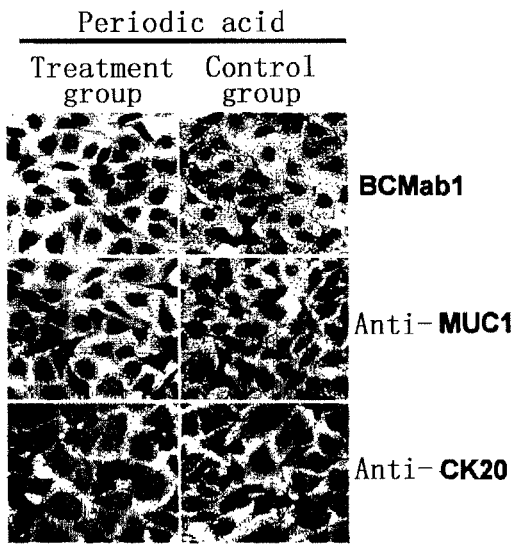
FIG. 2. Periodide-Oxidation Experiment (Experimental principle of the Periodic acid-Oxidation experiment: a hydroxyl group of the carbohydrate in glycoprotein is oxidized by a periodic acid in an acidic condition without any alteration of the polypeptide chain structure).
Figure 3:
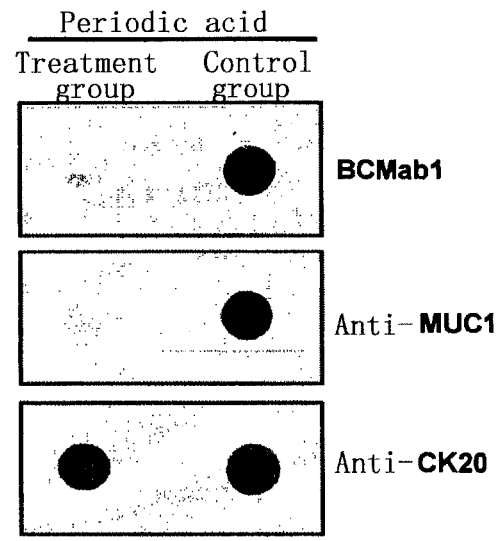
FIG. 3. Periodide-Oxidation Experiment (Dot blot hybridization experiment, with a result similar with FIG. 2). After lysis, bladder cancer cells T24 were spotted on a film and treated with iodic acid, so that the carbohydrate antigen structure was destroyed, carbohydrate antigen structure was not able to be detected by the antibody BCMab1 and no positive reaction was present.
Figure 4:
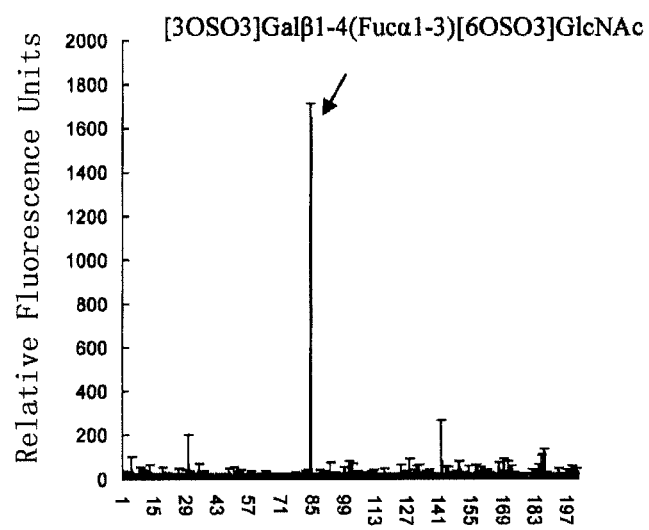
FIG. 4. Results of the carbohydrate chip assay.

Data were examined by periodate oxidation experiment (Daigo Tsubokawa, Yukinobu Goso, Akira Sawaguchi, et al. A monoclonal antibody, PGM34, against 6-sulfated bloodgroup H type 2 antigen, on the carbohydrate moiety of mucin. FEBS J. 2007 April; 274(7):1833-48) in combination with antibody-BCMab1 carbohydrate chips (The Consortium for Functional Glycomics, USA). The epitope recognized by antibody BCMab1 is a carbohydrate chain on human integrin α3β1, i.e. [3OSO3]Galβ1-4(Fucα1-3)[6OSO3]GlcNAc (see FIGS. 2, 3 and 4), an O-linked polysaccharide. And such a carbohydrate chain is located on amino acid T (threonine) at position 740 of α3 subunit (on the T in STSS). Since antibody BCMab1 specifically binds to human bladder cancer tissue only, the antigen is indicated to be integrin α3β1 modified by aberrant glycosylation (AG-α3β1), and its epitope [3OSO3]Galβ1-4(Fucα1-3)[6OSO3]GlcNAc is merely expressed in bladder cancer tissue cells. After identification, the structure of [3OSO3]Galβ1-4(Fucα1-3)[6OSO3]GlcNAc is shown below:

TABLE 2

Mass chromatographic identification of antigen of BCMab I

| Reference Scan(s) | Peptide | MH+ | z | Score XC | Coverage DeltaCn | MW Sp | Accession RSp | Peptide (Hits) Ions | Count |
|---|---|---|---|---|---|---|---|---|---|
| | integrin alpha 3 isoform b, precursor [Homo sapiens] | | | 98.30 | | 118756.8 | 600611 | 10 (9 1 0 0 0) | |
| 4184 | R.TGAVYLCPLTAHK.D | 1431.65517 | 2 | 3.44 | 0.40 | 817.8 | 1 | 16/24 | 1 |
| 4236 | R.YTQVLWSGSEDQR.R | 1569.65696 | 2 | 4.21 | 0.44 | 1330.6 | 1 | 20/24 | 1 |
| 4704 | R.YLLLAGAPR.E | 974.18150 | 2 | 3.14 | 0.44 | 1554.8 | 1 | 15/16 | 1 |
| 5265 | R.LQSFEGGTVIVIGESGM*K.T | 1692.93394 | 2 | 3.01 | 0.19 | 768.3 | 1 | 16/30 | 1 |
| 5304 | K.EAGNPGSLFGYSVALHR.Q | 1775.94547 | 2 | 3.88 | 0.57 | 1213.9 | 1 | 21/32 | 1 |
| 5550 | R.HMGAVFLLSQEAGGDLP.R | 1802.04787 | 2 | 5.98 | 0.57 | 3828.0 | 1 | 29/32 | 1 |
| 5600 | R.LQSFFGGTVMGESGMK.T | 1676.93902 | 2 | 4.26 | 0.49 | 1569.4 | 1 | 22/30 | 1 |
| 6376 | K.LELLLMDNLR.D | 1230.50277 | 2 | 3.48 | 0.26 | 1398.1 | 1 | 16/18 | 1 |
| 6582 | R.FAGSESAVFHGFFSMPEMR.C | 2135.41062 | 2 | 4.61 | 0.55 | 1509.1 | 1 | 21/36 | 1 |
| 5265 | R.LQSFFGGTVM*GESGMK.T | 1692.93394 | 2 | 2.45 | 0.48 | 581.1 | 2 | 15/30 | 1 |
| | integrin beta 1 ispform 1A precursor [Homo sapiens] | | | 130.31 | | 88415.9 | 19743823 | 13 (1 3 0 0 0 0) | |
| 3281 | K.SAVTIVVNPK.Y | 1016.17355 | 1 | 1.80 | 0.29 | 557.7 | 2 | 11/18 | 1 |
| 3692 | R.SNGLICGGNGVCK.C | 1336.46409 | 2 | 3.03 | 0.34 | 820.0 | 1 | 18/24 | 5 |
| 3705 | R.DKLPQPVQPDPVSHCK.E | 1846.07060 | 3 | 3.55 | 0.38 | 798.0 | 1 | 25/60 | 5 |
| 3800 | K.FCECDNFNCDR.S | 1537.55049 | 2 | 3.88 | 0.49 | 1769.6 | 1 | 18/20 | 5 |
| 4234 | K.LSEGVTISYK.S | 1097.24343 | 2 | 2.62 | 0.49 | 972.4 | 1 | 15/18 | 5 |
| 4454 | K.WDTGENPIYK.S | 1223.31587 | 2 | 2.82 | 0.45 | 688.0 | 1 | 15/18 | 1 |
| 5306 | R.IGFGSFVEK.T | 984.13002 | 2 | 2.42 | 0.37 | 548.6 | 1 | 12/16 | 5 |
| 5792 | K.SLGTDLMNEMR.R | 1267.45864 | 2 | 3.25 | 0.46 | 897.1 | 1 | 17/20 | 5 |
| 5979 | K.LKPEDITQIQPQQLVLR.L | 2020.36187 | 2 | 5.29 | 0.42 | 1561.2 | 1 | 23/32 | 5 |
| 6170 | K.NVLSLTNKGEVFNELVGK.Q | 1962.23605 | 2 | 6.14 | 0.55 | 2084.2 | 1 | 24/34 | 5 |
| 6318 | R.LLVFSTDAGFHFAGDGK.L | 1782.97638 | 2 | 4.78 | 0.62 | 1901.6 | 1 | 21/32 | 5 |
| 7665 | K.LSENNIQTIFAVTEEFQPVYK.E | 2471.74650 | 2 | 4.82 | 0.58 | 1352.7 | 1 | 24/40 | 5 |
| 8195 | R.AEDYPIDLYYLMDLSYSMK.D | 2331.64649 | 2 | 4.91 | 0.61 | 1340.6 | 1 | 22/36 | 5 |

Note: Sequence identifiers for the amino acid sequences of peptides shown in Table 2 are, for intergrin alpha 3 isoform b precursor [Homo sapiens], SEQ ID NO: 5 (scan 4184), SEQ ID NO: 6 (scan 4236), SEQ ID NO: 7 (scan 4704), SEQ ID NO: 8 (scan 5265), SEQ ID NO: 9 (scan 5304), SEQ ID NO: 10 (scan 5550), SEQ ID NO: 11 (scan 5600), SEQ ID NO: 12 (scan 6376), SEQ ID NO: 13 (scan 6582), and SEQ ID NO: 14 (scan 5265); and, for integrin beta 1 isoform 1A precursor [Homo sapiens], SEQ ID NO: 15 (scan 3281), SEQ ID NO: 16 (scan 3692), SEQ ID NO: 17 (scan 3705), SEQ ID NO: 18 (scan 3800), SEQ ID NO: 19 (scan 4234), SEQ ID NO: 20 (scan 4454), SEQ ID NO: 21 (scan 5306), SEQ ID NO: 22 (scan 5792), SEQ ID NO: 23 (scan 5979), SEQ ID NO: 24 (scan 6170), SEQ ID NO: 25 (scan 6318), SEQ ID NO: 26 (scan 7665), and SEQ ID NO: 27 (scan 8195).

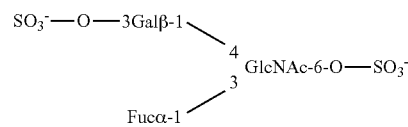

Detailed procedure of the periodate oxidation experiment are listed as follows: T24 cells were cultured in a 24-well plate for 24 hours. A pre-cooled paraformaldehyde solution (1 ml)

was added and kept for 15 min to fix the cells. T24 cells were oxidized by the high-iodine protein in a sodium-acetate balanced solution at room temperature for 1 hour. Excessive periodate was neutralized after cultured with sodium borohydride at room temperature for 30 min. T24 cells were stained immunohistochemically with antibodies BCMab1, anti-MUC1 or anti-CK20. The secondary antibody labeled with peroxidase and DAB assay kit were used for color development.

Detailed procedures of the carbohydrate chip experiment for antibody BCMab1 are shown as follows:

BCMab1 was diluted with 3% BSA/PBS buffer to a concentration of 1 μg/ml. To a carbohydrate chip, 100 μl BCMab1 diluention was added and incubated in a wet box for 1 hour. The glass slide was rinsed with 0.05% Tween 20/PBS (PBS-T), and incubated with 200 μl Cy5-linked goat anti-mouse IgG antibody (1:200) (Novocastra Laboratories Ltd, UK) in a wet box for 1 hour. The slide was dried in air, scanned to detect fluorescence at a wavelength of 635 nm using a microarray scanner (GenePix 4000B, Molecular Devices), and analyzed with the GenePix Pro software.

Figures 5, 6:
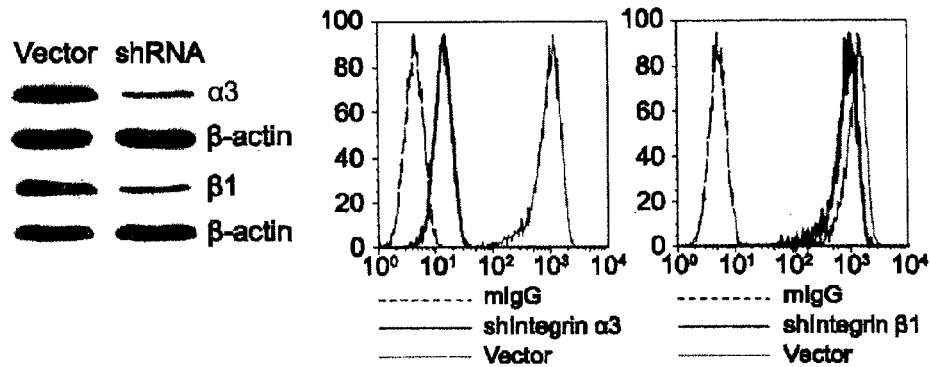
FIG. 5. Knockdown of integrin α3 or integrin β1 in T24 cells (Vector is a vector control, and β-actin is an internal standard for amplification)
FIG. 6. Integrin α3-knockdown T24 cells were barely stained by BCMab1, whereas integrin β1-knockdown T24 cells were stained (shIntegrin α3 and shIntegrin β1 represent the cells in which the α3 and β1 subunits are knocked down by RNAi, respectively)

The experiment for determining the specific position of the polysaccharide epitope recognized by BCMab1 in integrin α3β1 subunits is shown as follows: α3 or β1 subunit was knocked down by RNAi (through pSUPER-shIntegrinα3 or pSUPER-shIntegrinβ1 viral transfection). α3 or β1 subunit-silenced T24 cells and stable cell lines were screened by puromycin (FIG. 5). α3 or β1 could be knocked down by 80%. The α3 or β1 subunit-silenced T24 cells were stained by antibody BCMab1 and analyzed by FACS. The result showed that BCMab1 could not stain the α3-silenced T24 cells (FIG. 6, left), but stain the control cells with blank transfection and the β1-silenced T24 cells (FIG. 6, right). Mouse IgG (mIgG) (Sigma, Germany) was used as a negative control. In sum, the results showed that the site recognized by BCMab1 was in the α3 subunit.

The above FACS flow cytometry is shown as follow: first, a single-cell suspension was prepared, and stained on ice for 40 min by adding antibodies; the cells were washed with the PBS containing 0.1% BSA for 3 times, and incubated with FITC-labeled secondary antibody on ice for 40 min; after washing, an analysis was conducted using FACSCalibur flow analysis system (BD, US).

The detailed procedures for knocking down integrin α3β1 by RNAi are shown as follows: a small interfering RNA system acting on integrin α3 or β1 was established using pSUPER (Oligoengine, Washington, US) and then cloned into a pSUPER system, so as to express a 19 nt hairpin structure (shRNA) (comprising a small loop of 9 nt). The sequences encoding integrin α3 or β3shRNA are shown below:

The inserted shRNAs (pSUPER-shIntegrinα3, pSUPER-shIntegrinβ1) were confirmed in these DNA sequences. T24 cells were transfected by Lipofectamin2000 (Invitrogen, US). Integrin α3β1- and GALNT1-knockdown cells were screened out using puromycin. The cells transfected with empty vectors were used as a control.

The antigen AG-α3β1 according to the invention can also be prepared by the following standard protocol:

I. Preparation of affinity column

1. Activating 0.33 g CNBr-activated Sepharose 4B Fast Flow matrix with 40 ml of 1 mM HCl for 30 min, and washing it with Binding Buffer 1 (25 mM HEPES, 500 mM NaCl, pH 7.4) twice;
2. Adding 10 mg antibody BCMab1 for binding at room temperature for 1 h;
3. Centrifuging, and removing the supernatant; adding 40 ml Blocking Buffer (0.1M ethanolamine, pH 8.0) for blocking at room temperature for 2 h;
4. Centrifuging, removing the supernatant, loading the column, connecting to a AKTA machine (GE), and rinsing and balancing with Buffer A (25 mM Tris, 150 mM NaCl, pH 7.4), then ready for loading samples.

II. Cell collection, sample loading and elution

1. Collecting T24 or EJ cells, and lysing these cells with a lysis buffer (25 mM Tris, 150 mM NaCl, pH 7.4, 1 mM PMSF);
2. Loading the cell lysate solution, and washing with Buffer A till $OD_{280}$ does not change significantly;
3. Eluting the bound protein with Buffer B (25 mM Tris, 2M NaCl, pH 7.4).

III. Desalinization, purification through molecular sieve, and electrophoretic analysis in combination with mass spectrometric characterization (The first elution peak is AG-α3β1).

EXAMPLE 4

Influence of GAL3ST2 on Aberrant Glycosylation of Integrin α3β1 In Bladder Cancer Tissues In cells, generation of sulphated [3OSO3]Galβ1-4(Fucα1-3)[6OSO3]GlcNAc carbohydrate required GAL3ST (galactose: 3-O-sulfonyltransferase). GAL3ST, including 4 members i.e. GAL3ST1, GAL3ST2, GAL3ST3 and GAL3ST4, could move sulphates to the position Gal C-3. Surprisingly, compared with other members (GAL3ST1, GAL3ST3 and GAL3ST4), knockdown of GAL3ST2 (galactose: 3-O-sulfo-

```
5'-GATCCCCGCTACATGATTCAGCGCAATTCAAGAGATTGCGCTGAATCATGTAGCTTTTTA-3'    (SEQ ID NO: 28)
```

(α3, sense);

```
5'-AGCTTAAAAAGCTACATGATTCAGCGCAATCTCTTGAATTGCGCTGAATCATGTAGCGGG-3'    (SEQ ID NO: 29)
```

(α3, antisence).

```
5'-GATCCCCGCTGAAGACTATCCCATTGTTCAAGAGACAATGGGATAGTCTTCAGCTTTTTA-3'    (SEQ ID NO: 30)
```

(β1, sense);

```
5'-AGCTTAAAAAGCTGAAGACTATCCCATTGTCTCTTGAACAATGGGATAGTCTTCAGCGGG-3'    (SEQ ID NO: 31)
```

Figure 7:
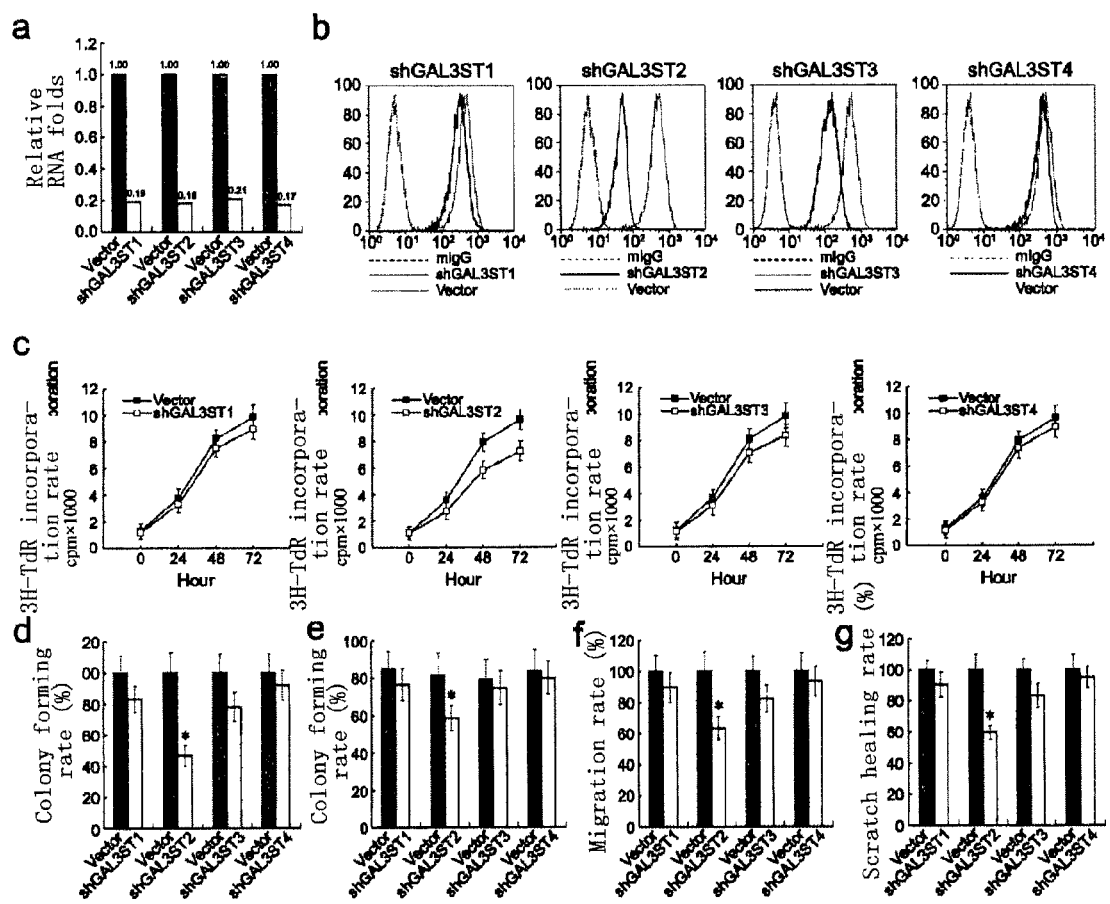
FIG. 7. Impact of GAL3ST2 on aberrant glycosylation of integrin α3β1 in bladder cancer tissues. (a) Puro-screening for GAL3ST1-4-silenced T24 cells and RT-PCR detection for the expression level. (b) BCMab1 barely stained GAL3ST2-knockdown cells. (c) Compared with the control cells transfected with an empty vector, knockdown of GAL3ST2 could reduce the proliferation of T24 cells significantly. (d) Knockdown of GAL3ST2 could reduce the colony forming ability of T24 cells significantly. (e) Knockdown of GAL3ST2 could reduce the adhesion of T24 cells significantly. (f, g) Knockdown of GAL3ST2 could reduce cell migration significantly.

(β1, antisence).

nyltransferase 2) could downregulate BCMab1 staining signal to a great extent (FIG. 7). Knockdown of GAL3ST2 could significantly inhibit the growth and migration of cancer. All these results suggested that GAL3ST2 played an important role in the aberrant glycosylation of integrin α3β1 in bladder cancer cells and carcinogenesis.

Knockdown of GAL3ST2 was conducted as follows. A small interfering RNA system acting on GAL3ST2 was established using pSUPER and then cloned into a pSUPER system, so as to express a 19 nt hairpin structure (shRNA) (comprising a small loop of 9 nt). The sequences encoding GAL3ST2 shRNA are shown below:

```
5'-GATCCCCCGGTCACCAACATCATGTTTTCAAGAGAAACATGATGTTGGTGACCGTTTTTA-3'  (SEQ ID NO: 32)

(GAL3ST2, sense);

5'-AGCTTAAAAACGGTCACCAACATCATGTTTCTCTTGAAAACATGATGTTGGTGACCGGG-3'  (SEQ ID NO: 33)

(GAL3ST2, antisense).
```

The inserted shRNAs (pSUPER-shGAL3ST2) were confirmed in these DNA sequences. T24 cells were transfected by Lipofectamin2000 (Invitrogen, US). GAL3ST2-knockdown cells were screened out using puromycin. The cells transfected with empty vectors were used as a control.

The sequences encoding GAL3ST1-, GAL3ST3- and GAL3ST4-knockdown shRNAs are listed below, and the experiments were carried out in the similar procedures with those conducted for the knockdown of GAL3ST2:

```
5'-GATCCCCTCCGAAACCTGCTCTTCTTTTCAAGAGAAAGAAGAGCAGGTTTCGGATTTTTA-3'  (SEQ ID NO: 34)

(GAL3ST1, sense);

5'-AGCTTAAAAATCCGAAACCTGCTCTTCTTTCTCTTGAAAAGAAGAGCAGGTTTCGGAGGG-3'  (SEQ ID NO: 35)

(GAL3ST1, antisence).

5'-GATCCCCGGTGCAGAACATCCTGTTTTCAAGAGAAAACAGGATGTTCTGCACCTTTTTA-3'  (SEQ ID NO: 36)

(GAL3ST3, sense);

5'-AGCTTAAAAAGGTGCAGAACATCCTGTTTTCTCTTGAAAAACAGGATGTTCTGCACCGGG-3'  (SEQ ID NO: 37)

(GAL3ST3, antisence).

5'-GATCCCCGGTGCAGAACATCCTGTTTTTCAAGAGAAAACAGGATGTTCTGCACCTTTTTA-3'  (SEQ ID NO: 38)

(GAL3ST4, sense);

5'-AGCTTAAAAATCCGCAAGTCACCATCTTTTCTCTTGAAAAGATGGTGACTTGCGGAGGG-3'  (SEQ ID NO: 39)

(GAL3ST4, antisence).
```

The detailed procedures for the above cell adhesion experiment are shown as follows:

Matrigel (BD, US) was coated on a 96-well plate, and blocked with 10 mg/ml thermally inactivated BSA for 1 hour. After becoming confluence, the above knockdown T24 cells were digested with 1% trypsin, collected at a concentration of $5×10^5$ cell/ml, resuspended in RPMI-1640 containing 1% FBS, and reconstituted at 37° C. for 15 min. shRNA vector was used as a control. The unadhered cells were rinsed off, whereas the adhered cells were collected and stained with 0.1% crystal violet (Sigma, Germany). After decoloration and dye solubilization, the samples were read at 575 nm by ELISA reader.

The detailed procedures for the above cell migration experiment are shown as follows:

Transwell experiment utilized optimized Boyden chemotaxis kit (with an pore size of 8 μm, Costar, US). Matrigel (100 μg/ml) was coated, and blocked with the PBS containing 1% BSA. The above knockdown T24 cells were digested with 1% trypsin, washed, and resuspended in a medium containing 1% BSA. The lower chambers contained 10% FBS or 1% BSA (negative control). After being incubated at 37° C. for 4 hour, the cells remained in the upper chambers were sucked out, and the cells transferred into the lower chambers were fixed with ethanol and stained with Giemsa. The cells that penetrated through the filter membrane were counted under a microscope. Mitomycin C (2 μg/m) was used to inhibit cell proliferation.

EXAMPLE 5

N-Acetyl-Galactosaminyltransferase 1 (GALNT1) was Highly Expressed in Bladder Cancer Tissues and its Knockdown Line Downregulated Integrin α3β1 Glycosylation In order to confirm the function of glycosyltransferase in glycosylation of integrin α3β1, patients suffered from bladder cancer and normal bladder tissues were analyzed by DNA microarray. mRNA samples were obtained from 10 earlystaged patients and 10 normal persons through bladder biopsy. It was shown in the microarray analysis that GALNT1 mRNA level was higher in tumor tissues than normal tissues by 11.2 folds (Table 3). In contrast, the levels of other GALNTs (GALNT2-9) and fucosyltransforases (FUT 1-10) did not show significantly difference between bladder cancer tissues and normal tissues (Tables 3 and 4). No significant difference existed in respect of the to expression of α3 and β1 subunit mRNAs either. Housekeeping gene GAPDH was used as a control.

The microarray expression analysis is shown as follows detailedly. Total RNA was extracted by isopropanol/chloroform and Trizol from the bladder cancer tissues freshly dissected from 10 cases of patients and 10 cases of normal people. The investigation was carried out using human gene chips containing 35000 genes/chip (Catalog #: 220020; Product Name: CrystalCore human genomewide oligonucleotid microarry chip V2.0; Manufacturer: CapitalBio Corporation). Probes were obtained from 350 μg total RNA of the 10 cases of patients and 10 cases of normal people. cDNA probes were prepared and labeled using CyScribe First-Strand cDNA labeling kit (Amersham Biosciende, US). The bladder cancer tissue specimens were labeled with Cy3; whereas the normal specimens were labeled with Cy5. The labeled cDNA probes were mixed with 2.5×SSC, 0.2% SDS, and 15 μg PolyA RNA. The microarray chips were hybridized at 50° C. for 16 hours, and analyzed by ScanArray 4000 Microarray Analysis System (Packkad Bioscience, US). The data were analyzed by Microarray Analysis Software (Dapple version 0.68 beta).

TABLE 3

High expression of GALNT1 in bladder cancer tissues

| GenBank No. | Gene name | Normal bladder tissues | | Bladder tumor tissues | | |
| --- | --- | --- | --- | --- | --- | --- |
| | | Signal$^{\times}$ | Detection$^{\S}$ | Signal$^{\times}$ | Detection$^{\S}$ | Fold-change$^{\#}$ |
| NM_020474 | GALNT 1 | 303 ± 26 | P | 3384 ± 142 | P | 11.2 |
| NM_004481 | GALNT 2 | 748 ± 23 | P | 703 ± 35 | P | 0.9 |
| NM_004482 | GALNT 3 | 1854 ± 72 | P | 1315 ± 118 | P | 0.7 |
| NM_003774 | GALNT 4 | 36 ± 3 | A | 42 ± 7 | A | 1.2 |
| NM_014568 | GALNT 5 | 12 ± 1 | A | 16 ± 1 | A | 1.3 |
| NM_007210 | GALNT 6 | 815 ± 39 | P | 902 ± 45 | P | 1.1 |
| NM_017423 | GALNT 7 | 735 ± 43 | P | 836 ± 72 | P | 1.1 |
| NM_017417 | GALNT 8 | 87 ± 9 | A | 107 ± 23 | A | 1.2 |
| NM_021808 | GALNT 9 | 172 ± 26 | A | 166 ± 18 | A | 0.9 |
| NM_002204 | Integrin alpha-3 | 3179 ± 112 | P | 3026 ± 137 | P | 0.9 |
| NM_033666 | Integrin beta-1 | 2877 ± 58 | P | 2800 ± 64 | P | 1.0 |
| NM_002046 | GAPDH | 80942 ± 294 | P | 81409 ± 367 | P | 1.0 |

Gene expression profile of human normal bladder tissues, and bladder tumor tissues.
Abbreviations:
A, absent;
P, present.
$^{\times}$Calculated mean fluorescence intensity signal.
$^{\S}$Classification of gene expression as absent or present.
$^{\#}$Proportion of the signals from experiments with bladder tumor tissues to normal bladder tissues for genes with changed expression (fold change >1 for increased and <1 for decreased gene expression).

TABLE 4

No significant difference of fucosyltransforase (FUT) expression in bladder cancer cells and in normal bladder tissues

| GenBank No. | Gene name | Normal bladder tissues | | Bladder tumor tissues | | |
| --- | --- | --- | --- | --- | --- | --- |
| | | Signal$^{\times}$ | Detection$^{\S}$ | Signal$^{\times}$ | Detection$^{\S}$ | Fold-change$^{\#}$ |
| NM_000148 | FUT 1 | 1836 ± 132 | P | 1684 ± 127 | P | 0.9 |
| NM_000511 | FUT 2 | 368 ± 26 | P | 403 ± 37 | P | 1.1 |
| NM_000149 | FUT 3 | 2734 ± 192 | P | 2835 ± 185 | P | 1.0 |
| NM_002033 | FUT 4 | 593 ± 35 | P | 502 ± 47 | P | 0.8 |
| NM_002034 | FUT 5 | 18 ± 3 | A | 23 ± 5 | A | 1.3 |
| NM_000150 | FUT 6 | 1253 ± 29 | P | 1392 ± 54 | P | 1.1 |
| NM_004479 | FUT 7 | 685 ± 73 | P | 823 ± 67 | P | 1.2 |
| NM_178156 | FUT 8 | 406 ± 35 | P | 378 ± 19 | P | 0.9 |
| NM_006581 | FUT 9 | 82 ± 16 | A | 96 ± 23 | A | 1.2 |
| NM_032664 | FUT 10 | 1358 ± 126 | P | 1407 ± 164 | P | 1.0 |
| NM_002046 | GAPDH | 80942 ± 294 | P | 81409 ± 367 | P | 1.0 |

Gene expression profile of human normal bladder tissues and bladder tumor tissues.
Abbreviations:
A, absent;
P, present.
$^{\times}$Calculated mean fluorescence intensity signal.
$^{\S}$Classification of gene expression as absent or present.
$^{\#}$Proportion of the signals from experiments with bladder tumor tissues to normal bladder tissues for genes with changed expression (fold change >1 for increased and <1 for decreased gene expression).

T24 cells were transfected with pSUPER-shGALNT1 vectors, so as to downregulate GALNT1 expression. The GALNT1-knockdown T24 cell lines that had been transfected stably were screened out using puromycin (FIG. 8). GALNT could be silenced by 80%. Compared with empty pSUPER vector, the GALNT1-knockdown cell lines could downregulate BCMab1 staining signal significantly (FIG. 9, left). A competitive inhibition experiment was conducted to the substrate BG of GALNT1. In the BG experiment, signal of integrin α3β1 recognized by BCMab1 was downregulated (FIG. 9, right). mIgG was the negative control. The result showed that GALNT1 might induce aberrant methylation of the integrin α3β1 in bladder cancer.

The method for silencing GALNT1 is shown below. A small interfering RNA system acting on GALNT1 was established using pSUPER and then cloned into a pSUPER system, so as to construct a pSUPER-shGALNT1 vector and express a 19 nt hairpin structure (shRNA) (comprising a small loop of 9 nt). The sequences encoding GALNT1 shRNA are shown below:

5'-GATCCCCCCAGTACAAAAGCCTCATGTTCAAGAGACATGAGGCTTTTGTACTGGTTTTTA-3' (SEQ ID NO: 40)

(GALNT1, sense);

5'-AGCTTAAAAACCAGTACAAAAGCCTCATGTCTCTTGAACATGAGGCTTTTGTACTGGGGG-3' (SEQ ID NO: 41)

(GALNT1, antisence).

The inserted shRNAs (pSUPER-shGALNT1) were confirmed in these DNA sequences. T24 cells were transfected by Lipofectamin2000 (Invitrogen, US). GALNT1-knockdown cells were screened out using puromycin. The cells transfected with empty vectors were used as a control.

GALNT1 was inhibited by BG. T24 cells were cultured in a 6-well plate with or without 2 mM BG (Sigma, Germany) for 7 days. The cells were collected, into which BCMab1 and its corresponding FITC-linked secondary antibody were added and incubated for 40 min. The expression of antigen of BCMab1 was analyzed by FACS.

EXAMPLE 6

Knockdown of Integrin α3 or GALNT1 can Inhibit Cancer Proliferation and Tumor Growth Knockdown of integrin α3 or GALNT1 (see above for the detailed procedures) could significantly reduce the binding rate between [$^3$H]-thymidine and DNA of T24 cells (FIG. 10, a), and remarkably affect the cloning of T24 cells (FIG. 10, b). In order to investigate the influence of the knockdown of integrin α3 or GALNT1 on tumors in vivo, a tumor-bearing model was constructed by inoculating BALB/c nude mice at their backs subcutaneously, then tumor change was observed by injecting vectors. Compared with the control group, the integrin α3- or GALNT1-knockdown group significantly inhibited growth of the subcutaneous tumors (FIG. 10, c). And by the end of the observation period, i.e. on Day 35, the tumor inhibition ratio reached 63% and 42%, respectively.

The steps of the cell proliferation experiment are shown as follows. $^3$H nuclide incorporation assay was utilized. Wildtype T24 cells and shIntegrin α3- or shGALNT1-knockdown T24 cells ($2 \times 10^3$ cells/well) were coated onto a 96-well plate and cultured till reaching 70%-80% confluence. The cells were cultured in serum-free RPMI-1640 for 24 hours and the medium was replaced by RPMI-1640 containing 10% FBS. To the wildtype T24 cells, 10 μg/ml of BCMab1 or control mIgG was added. After 72 hours, $^3$H was added and the cells were cultured for 4 hours. Then the cells were collected and detected for $^3$H incorporation amount by a liquid scintillation counter LKB1219.

The above animal experiment was shown below. BALB/c nude mice (female, 6 weeks old, with a body weight of about 15 g) (purchased from Chinese Academy of Medical Science Institute of laboratory animal) were fed in a SPF environment. T24 cells (including wildtype T24 cells and shIntegrin α3- or shGALNT1-knockdown T24 cells) were xenografted, and tumor cells ($1 \times 10^7$, suspended in PBS) were injected subcutaneously at their backs. When tumors grew up to 3-5 mm, the mice with wildtype T24 were grouped (10 per group), and BCMab1 or mIgG (10 mg/kg) was injected intraperitoneally, 3 times/week, for 35 days. The tumor volumes were measured twice per week. Orthotopic bladder cancer transplantation model, T24 cells were labeled with GFP, and tumors were induced to be transplanted into bladders by blood vessel probes. BCMab1 or mIgG (1 mg/kg) was administered into the bladders of 24 mice in each group. The images were obtained by an in vivo imaging system (IVIS) on days 5, 10, 15, 20, 25 and 30 after transplantation.

EXAMPLE 7

Figure 11:
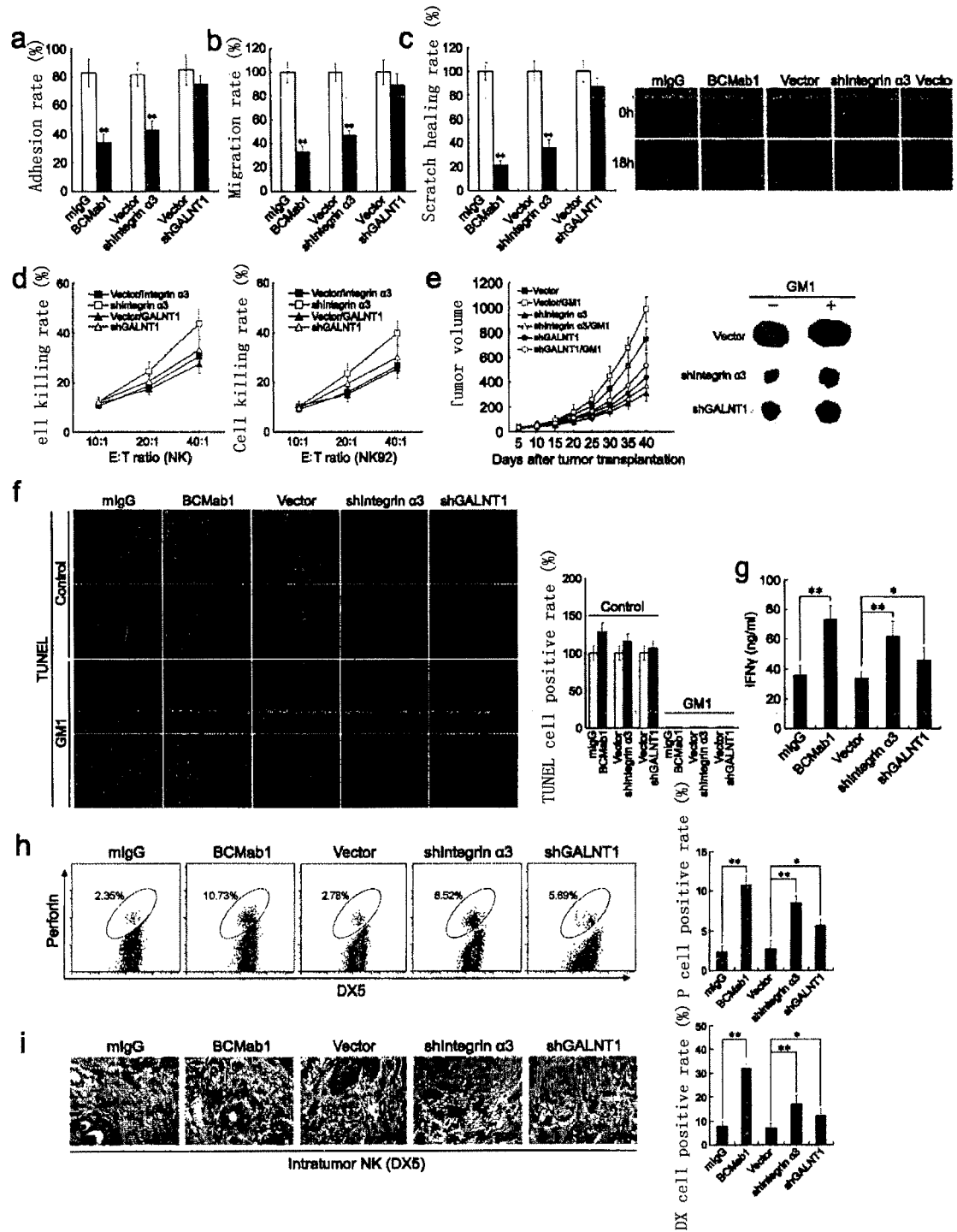
FIG. 11. Knockdown of integrin α3 inhibited the adhesion between tumor and extracellular matrix (ECM) and tumor migration, as well as facilitated NK cell-mediated cell killing. (a, b) Compared with an empty vector, knockdown of integrin α3 weakened the adhesion between tumors and ECM (a) and tumor migration (b) (p<0.01); whereas knockdown of GALNT1 failed to show an evident result. BCMab1 (10 μg/ml) could inhibit cell junction and tumor migration significantly (mIgG as negative control). (c) It was confirmed in a scratch test that knockdown of integrin α3 could inhibit migration of tumor cells (p<0.01). (d) Silence of integrin α3 or GALNT1 could improve the cell killing caused by NK cells. $^{51}$Cr-labeled integrin α3 or GALNT1-silenced EJ cells and IL-2-activated NK cells (left) or NK92 cells (right) were incubated together at 37° C. for 4 hours in various effect-target ratios (E/T). (e) Integrin α3 or GALNT1-knockdown cells were inoculated into the mice from which NK cells had been removed, and the growth of tumor cells was accelerated. NK cells were removed using anti-asialo GM (GM) antibody, and then the integrin α3 or GALNT1-knockdown EJ cells were inoculated. Tumor volumes were measured periodically, and averaged (the left panel). The tumor status on Day 35 is shown in the right panel. (f) Removal of NK cells impacted tumors. After a TUNEL staining (left), the average numbers of the positively stained cells were calculated (the right panel). (g, h) Tumors inoculated with integrin α3-/GALNT1-knockdown EJ cells or BCMab1-treated EJ cells, compared with tumors inoculated with EJ cells transfected with an empty vector or mIgG-treated EJ cells, could significantly facilitate the secretion of IFNγ and perforin by NK cells. IFNγ was detected by ELISA and perforin was detected by FACS. (i) Tumors inoculated with integrin α3-/GALNT1-knockdown EJ cells or BCMab1-treated EJ cells, compared with tumors inoculated with EJ cells transfected with an empty vector or mIgG-treated EJ cells, could facilitate the recruitment of NK cells inside tumors.

Knockdown of Integrin α3 or GALNT1 can Inhibit Cancer Proliferation and Tumor Growth The detailed procedures for knockdown of integrin α3 or GALNT1 are described in the previous Examples. The function of the integrin α3- or GALNT1-knockdown T24 cells was detected. It was found that α3-knockdown T24 cells could significantly inhibit adhesion between cells and Matrigel (FIG. 11, a). The migration experiment indicated that α3-knockdown T24 cells significantly inhibited cell migration (FIG. 11, b). The scratch test (Huang, J., et al. Genetic and epigenetic silencing of SCARAS may contribute to human hepatocellular carcinoma by activating FAK signaling. J Clin Invest 120, 223-241 (2010)) showed similar results (FIG. 11, c). However, knockdown of GALNT1 did not impact cell adhesion or migration significantly (FIG. 11, a~c), suggesting that silence of integrin α3 could inhibit adhesion and migration of bladder cancer cells.

EXAMPLE 8

Knockdown of Integrin α3 or GALNT1 can Enhance NK Cell-mediated Lysis of Bladder Cancer Cells The detailed procedures for knockdown of integrin α3 or GALNT1 are described in the previous Examples. We investigated the killing action of nature killer (NK) cells against integrin α3- or GALNT1-knockdown T24 cell lines. Compared with the empty vector controls (Vector/integrin α3 and Vector/GALNT1), the knockdown cell lines could enhance the killing action of NK cells (extracted from peripheral blood of healthy human). In the experiment for testing the killing action of NK cells against α3-knockdown cell lines, where E/T (effector cell/target cell) ratios were 10:1, 20:1, and 40:1, the killing activities of NK cells against α3 knockdown and empty vector controls were 12.5±1.6% vs 10.8±0.6% (p=0.106), 24.6±3.9% vs 18.5±2.1% (p=0.001), and 43.8±5.4% vs 30.7±2.7%, respectively (p<0.001) (FIG. 11, d, left). In the experiment for testing the killing action of NK cells against GALNT1-knockdown cell lines, the killing activities were 12.4±0.8% vs 11.7±1.4% (p=0.439), 20.5±2.1% vs 17.3±2.3% (p=0.017), and 33.2±4.4% vs 27.6±3.7% (p<0.002), compared with controls. In conclusion, knockdown of α3 could activate NK cell-mediated killing action more effectively, compared with knockdown of GALNT1. And similar results were achieved for NK92 cell (ATCC: CRL-2407) mediated killing action (FIG. 11, d, right).

To further study the killing action of NK cells against tumor cells, the NK cells were eliminated by anti-asialo GM1 antibody (Wako Chemicals, Richmond, Va.) in BALB/C mice before inoculation of T24 cells. In this model, integrin α3- or GALNT1-knockdown T24 cells could significantly inhibit growth of tumors, compared with empty vectors. No died cell was found in the tumor tissues of α3- or GALNT1-T24-inoculated mice from which NK cells had been eliminated (FIG. 11, f); whereas a few died cells were observed in the early-stage tumor tissues from which NK cells had not been eliminated. Interestingly, in the tumors of the mice inoculated with α3-/GALNT1-T24, NK cells could significantly facilitate the expression of perforin and IFNγ (FIG. 11, g, h). Moreover, the number of the NK cells was greater in shIntegrin α3 or shGALNT1-treated tumors than in the control group (FIG. 11, i). The data suggested that the killing action mediated by NK cells played an important role in the tumor-bearing mouse with α3- or GALNT1-knockdown T24.

EXAMPLE 9

Antibody BCMab1 Inhibited Proliferation of Tumor Cells

T24 cells were inoculated into a 96-well plate in a density of 1×10³ cells/well, and cultured conventionally till reaching the confluence of 70-80%. Then the cells were starved in a serum-free medium for 24 hours. Antibody BCMab1 (100 μg/mL) was added, and the culture was continued for 48 hours while serum was resumed. At the same time, homogenic mouse IgG (mIgG (Sigma, Germany)) was used as a control. The cells were incubated with the incorporation of [³H]-TdR (synthesized by Isotope Institute of China Institute of Atomic Energy) for 4 hours, and counted for the amount labeled by [³H]-TdR using a liquid scintillation counter LKB1219 (LKB Corporation, Sweden). As shown in FIG. 12, the result indicated that compared with the control group, the proliferation of tumor cells was inhibited significantly in the antibody BCMab1-treated group.

Example 10

Figure 15:
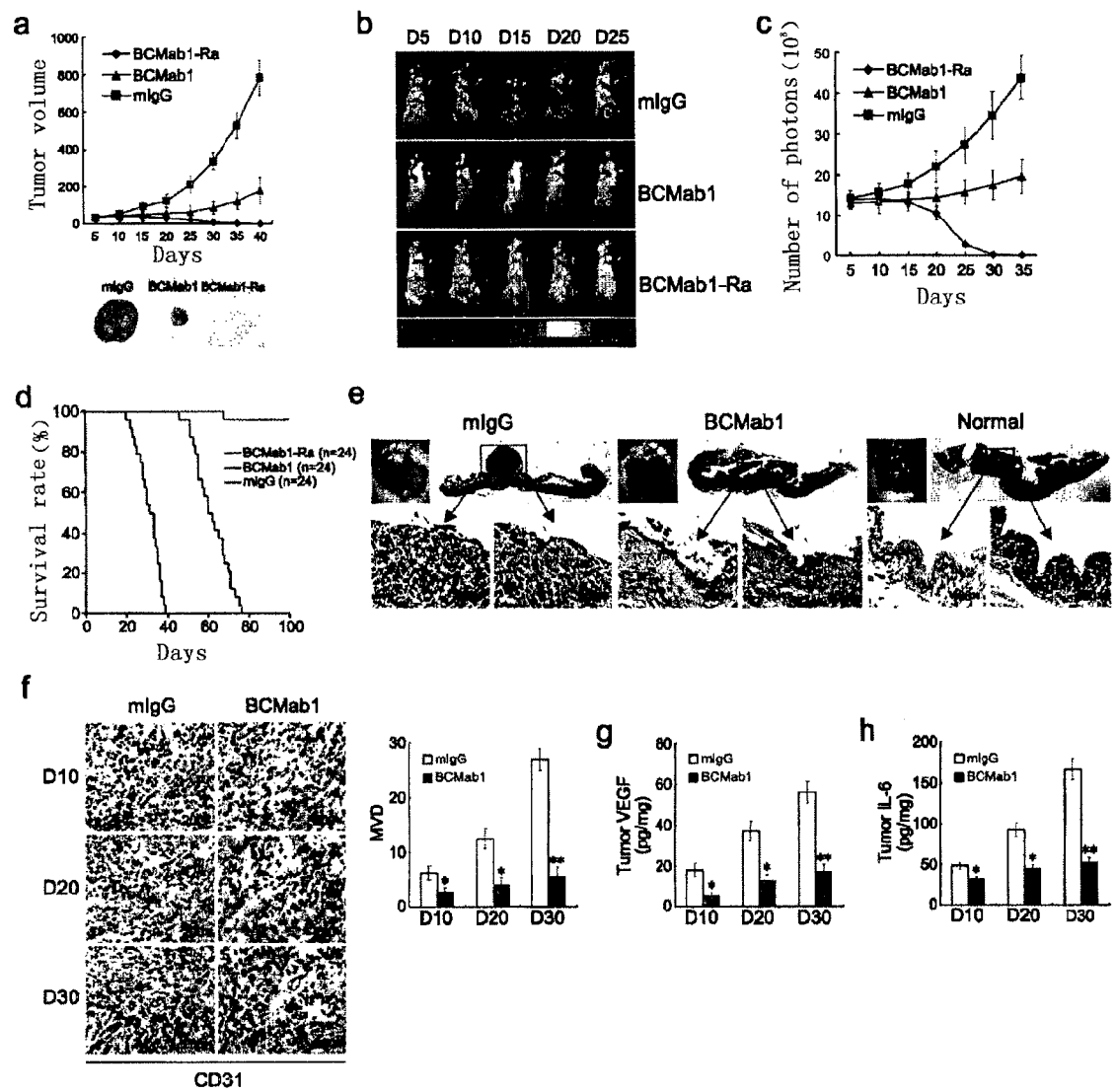
FIG. 15. BCMab1 and BCMab1-Ra inhibited growth of the transplanted tumors of a mouse-borne tumor model. (a) In a xenografted mouse-borne tumor model, BCMab1 and BCMab1-Ra inhibited cancer growth. T24 cells were injected into nude mice subcutaneously. When the tumor diameter reached 3-5 mm, the mice were grouped (10 mice/group), and injected with BCMab1 or BCMab1-Ra (10 mg/kg) intraperitoneally, 3 times/week, for 5 weeks. The tumor statue on Day 35 is shown in the lower panel. (b) The tumor-suppression effect of BCMab1 and BCMab1-Ra on orthotopically transplanted bladder cancer. After transplanted, GFP-labeled T24 cells were imaged by IVIS on Days 5, 10, 15, 20 and 25. Chromatic aberration showed photon amounts of the mice. Groups of mice (24 mice/group) were administered by infusing bladder, and then given with BCMab1, BCMab1-Ra and mIgG (1 mg/kg each) respectively on the next day. (c) The growth curve of the orthotopic tumor after IVIS treatment. (d) Comparison of the growth curves for BCMab1, BCMab1-Ra and mIgG treated groups. (e) It was shown by immunohistochemisty and HE staining that injection of BCMab1 and BCMab1-Ra in bladder successfully inhibited tumor growth. The tumor was taken to a histological analysis on Day 25 during the treatment. No tumor cell was detected in BCMab1-Ra-treated mice. (f) BCMab1 downregulated the microvessel density (MVD) in tumors. BCMab1 and mIgG-treated mice were subjected to an immunohistochemistry assay using anti-CD31 antibody on Days 10, 20 and 30, so as to calculate MVD (measure microvessel density) (the right panel). (g, h) ELISA results showed that levels of VEGF and IL-6 in tumors were downregulated significantly in the BCMab1-treated mice.

BCMab1 and BCMab1-Ra Inhibited Growth of Subcutaneous and Orthotopic Bladder Cancer Models As shown in FIGS. 10 and 11, BCMab1 could significantly inhibit the growth of bladder tumors, colony formation and migration. For the sake of confirming the anti-tumor function of BCMab1 in vivo, a xenograft tumor model was established by injecting T24 cells (1×10⁷, suspended in PBS) into the backs of BALB/c nude mice. When tumors grew up to a diameter of 0.3~0.5 cm, BCMab1 or control mIgG antibody (10 mg/kg) was injected intraperitoneally, 3 times/week. Compared with the control, tumors were reduced significantly in the BCMab1-treated group (FIG. 15, a). And the inhibition ratio reached 77% by the end of the experiment (Day 40).

To detect the orthotopic anti-tumor function of BCMab1, orthotopic transplantation tumor model of bladder cancer was built up using GFP fluorescence labeled T24 cells (GFP-T24). GFP-T24 (5×10⁶) cells were transplanted into bladder. GFP was detected by an in vivo imaging system (IVIS), so as to confirm that all the inoculated BALB/c nude mice were suffered from bladder cancer. The mice were grouped (24/group). BCMab1 or mIgG 1 mg/kg was injected into bladders (FIG. 15, b). Compared with the control group, administration of BCMab1 in bladder effectively inhibited growth of bladder cancer and extended lift time of T24 tumor-bearing mice (p<0.0001) (FIG. 15, c, d). No BCMab1-related toxicity was found in the experiment. And no metastasis was found in the BCMab1-treated group by histopathological investigation. However, in the mIgG control group, tumor metastasis was present in 30%~50% mice, tumors metastasized to lungs and lymph nodes, and 10% mice died (data not shown).

Immunotoxin BCMab1-Ra was generated through the conjugation between BCMab1 and ricin A chain. More specifically, ricin A chain and BCMab1 were connected via a heterogeneous difunctional crosslinking agent SPDP (N-succinimidyl 3-(2-pyridyldithiol)propionate) into the immunotoxin BCMab1-Ra. The detailed procedure was shown as follows.

1. Reaction (RT-PDP) Between Ricin A Chain (Ra) and Crosslinking Agent (SPDP):
   (1) 10 mg/3.5 ml Ra (prepared in accordance with: Song, P et al., The preparation of conjugate composed of ricin A chain and mAB 3G11 and the evaluation of its biological activity in vitro, Journal of Chinese Hospital Pharmacy, Vol. 25, No. 10, p899-901, 2005) was added to 100 μl 4 mg/ml SPDP (Sigma-Aldrich Co. LLC.) (dissolved in absolute ethanol, formulated immediately before use) in a 10-fold excessive molar ratio, and agitated at room temperature for 30 min;
   (2) A small amount of precipitate was observed after agitation, and then centrifuged at 10000 rpm for 30 seconds;
   (3) The supernatant was collected and placed into a dialysis bag (Beijing Xin Jing Ke Biotechnology Co. Ltd (MD44120)), then dialyzed with acetate buffer (0.02M/pH 4.5) overnight;
   (4) A small amount of precipitate was observed during the dialysis, and removed by centrifugation; the remaining solution was Ra-PDP solution.
2. Reaction (Ra-SH) Between Ra-PDP and DTT
   (1) 27 mg DTT (Sigma-Aldrich Co. LLC.) (with a final concentration of 50 mM) was added to 3.5 ml Ra-PDP, and agitated at room temperature for 30 min;
   (2) A small amount of precipitate was observed after agitation, and then centrifuged at 10000 rpm for 30 seconds;
   (3) The supernatant was collected and placed into a dialysis bag (Beijing Xin Jing Ke Biotechnology Co. Ltd (MD44120)), then dialyzed with PBS (containing 0.15M NaCl, 0.02M/pH 7.4) repeatedly till smellless.
3. Reaction (BCMab1-PDP) Between Antibody (BCMab1) and Crosslinking Agent (SPDP):
   (1) 5 mg/6.5 ml antibody was added to 30 μl of 4 mg/ml SPDP (dissolved in absolute ethanol, formulated immediately before use) in a 10-fold excessive molar ratio, and agitated at room temperature for 30 min;

(2) A small amount of precipitate was observed after agitation, and then centrifuged at 10000 rpm for 30 seconds;

(3) The supernatant was collected and placed into a dialysis bag, then dialyzed with PBS (containing 0.15M NaCl, 0.02M/pH 7.4).

4. Conjugation of Immunotoxin (BCMab1-Ra):

(1) 3.5 ml Ra-SH and 6.5 ml BCMab1-PDP were mixed (10 ml), and agitated at room temperature overnight (more than 16 hours);

(2) Obvious turbidity was observed, and centrifuged at 10000 rpm for 1 min;

(3) The samples were concentrated by PEG20000 into a loading volume of 5 ml and loaded onto a G-100 column (Beijing Xin Jing Ke Biotechnology Co. Ltd (3098));

(4) Each eluting peak was collected after loading samples (eluant: PBS (containing 0.15M NaCl, 0.02M/pH 7.4)), wherein the first peak was immunotoxin BCMab1-Ra, the second peak was antibody, and the third peak was toxin; measurement results showed immunotoxin $OD_{280}$=0.116, i.e. 5.1 mg/22 ml;

(5) immunotoxin was filtered for sterilization, and then kept at 4° C. or frozen/stored at −20° C.

The detailed steps are shown as follows:

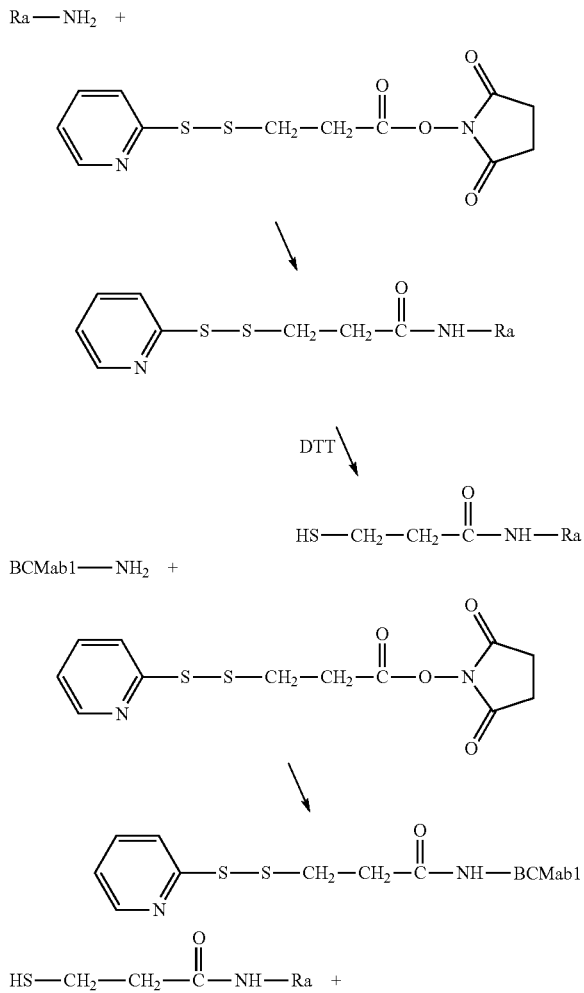

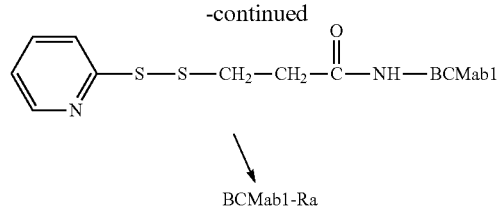

It was shown in indirect immunofluorescence, FACS analysis and competitive binding experiments that the binding activity between the antibody and immunotoxin was 95% of the initial activity. The cell culture suggested that BCMab1-Ra was a very effective biological agent capable of killing bladder cancer cell lines (EJ and T24). BCMab1-Ra could inhibit the proliferation and growth of human bladder cancer cell lines in vitro (data not shown). Interestingly, direct infusion of BCMab1-Ra into bladders through urethral injection could inhibit tumor growth in mouse orthotopic transplantation tumor model which had the same survival rate as normal mice (FIG. 15, b-d). No toxicity caused by BCMab1-Ra was observed. As a result, BCMab1-Ra can be used as a potential toxic medicament for the treatment of bladder cancer.

Twenty-five sites were detected in the bladder of a mouse, so as to determine whether bladder cancer was induced. Through IVIS detection of GFP fluorescence, it was found that all mice were suffered from bladder cancer. On Day 25 during the treatment, all tumors disappeared in the BCMab1 group (FIG. 15, e, middle). The immunohistochemical and HE staining results showed that only a few cancer cells remained at the inoculation sites of T24 cells; and no tumor cell was detected in the BCMab1-Ra-treated group immunohistochemically (data not shown). However, the tumors did not disappear in the mIgG control group (FIG. 15, e, left). No appreciable damage was observed on the bladder mucous membranes of the mice in both BCMab1 and BCMab1-Ra groups (FIG. 15, e). Neither of them showed any difference in the bladder mucous membranes from normal mice under microscope. Overall, BCMab1 could inhibit growth of bladder cancer in vivo, and a part of mice, without any severe side effect, were healed completely. In our experiments, BCMab1-Ra also could eliminate bladder cancer cells without causing side effect.

In order to further investigate whether BCMab1 impacts other cells in a microenvironment of tumor, we detected microvessel density (MVD) and cytokines such as VEGF and IL-6 in a tumor-bearing mouse model. In the BCMab1 treatment group, the number of MVD was reduced significantly (FIG. 15, f), generation of VEGF and IL-6 was inhibited in tumors (FIG. 15, g, h). Same results were shown in the BCMab1-Ra treatment group as well (data not shown). It was suggested that BCMab1 could also suppress angiogenesis while inhibiting proliferation of tumors.

Figure 16:
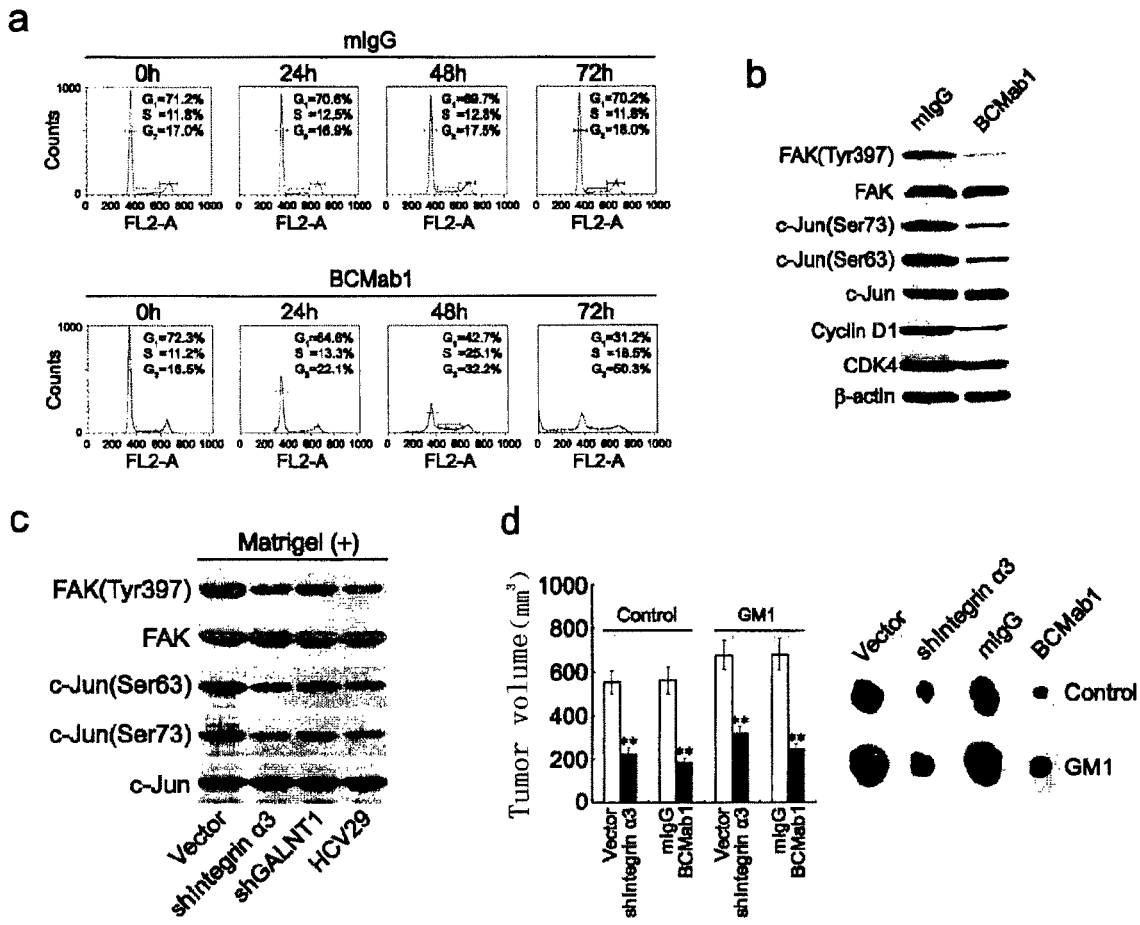
FIG. 16. BCMab1 resulted in cell cycle arrest and inhibited tumor growth. (a) BCMab1 resulted in cell cycle arrest. BCMab1 (10 μg/ml)-treated T24 cells were analyzed by a PI (Propidium Iodide)-staining flow cytometer. mIgG was used as a negative control. (b) Antibody BCMab1 inhibited phosphorylation of FAK and c-Jun, and downregulated expression of cyclin D1 and CDK4. The lysate was immunoblotted by anit-phospho-FAK (Tyr397) and anti-phospho-c-Jun (Ser63 and Ser73) as well as the total FAK and c-Jun. At the same time, the expression of cyclin D1 and CDK4 was detected. β-actin was used a control. (c) Aberrant glycosylation of integrin α3β1 enhanced the activation of FAK signal pathway. T24 cells and integrin α3- or GALNT1-silenced T24 cells were treated with Matrigel in a serum-free condition for 30 min. HCV29 cells were used as a normal control. (d) In NK cell-absent mice, BCMab1 still could inhibit tumor growth. After removal of NK cells using anti-asialo GM1 (GM1) antibody, the mice were administered with BCMab1, or inoculated with Integin α3-knockdown T24 cells. On Day 35, tumor volumes were measured, and averaged (the left panel). The right panel shows the tumor tissues.

Furthermore, we conducted some researches on the anti-tumor molecular mechanism of BCMab1, and found that BCMab1 could cause stasis of tumor cell cycles by preventing focal adhesin kinase (FAK) and c-Jun from phosphorylation (FIG. 16, a, b). The glycosylated α3β1 on T24 cells enhanced FAK-dependent signalings (FIG. 16, c). Knockdown of integrin α3 or GALNT1 lowered the phosphorylation levels of FAK and c-Jun significantly. In the case that NK cells were removed, BCMab1 still could inhibit growth of cancer (FIG. 16, d). All these results suggested that BCMab1 could inhibit tumor growth and improve the killing function of NK cells.

The above signal pathway experiment is shown as follows. T24 cells were starved in serum-free RPMI-1640 for 24 hours, and then cultured in RPMI-1640 containing 10% FBS and 10 μg/ml BCMab1 or mIgG control. After 48 hours, the cells were lysed with lysis buffer. The lysate supernatant was analyzed by immunodotting with anti-human FAK, FAK, Phospho-FAK (Tyr397), c-Jun, Phospho-c-Jun (Ser63), Phospho-c-Jun (Ser73), CyclinD1 or CDK4 antibodies.

The antibodies used in the above experiments include: rabbit anti-human CyclinD1, rabbit anti-human CDK4, rabbit anti-human c-Jun, Phospho-c-Jun (Ser63), Phospho-c-Jun (Ser73), rabbit anti-human FAK, Phospho-FAK (Tyr397) (CST, US), and homotypical control mIgG (Sigma, Germany). Mouse monoclonal antibody BCMab1 was isolated from ascites using Protein A Sepharose. The biotinylatd HRP and FITC labeled secondary antibodies were purchased from Pierce, US and Sigma, Germany, respectively.

Integrins impacted the adhesion-related effects in tumor cells, including proliferation, survival, migration, invasion and passage of FAK signal pathway. Phosphorylation of FAK was deemed as one of the major steps realizing further phosphorylation of Src and Fyn and triggering of signal pathway. Glycosylation of integrin α3β1 was clearly different in tumor cell lines and in the control cell line. The connection between cells and extracellular matrix protein was modulated by glycosylation. We found that knockdown of integrin α3 or GALNT1 could inhibit proliferation of cancer and growth of tumors in vivo and in vitro. Suppression of integrin α3β1 signaling by BCMab1 also could inhibit proliferation of cancer and growth of tumors in vivo and in vitro. BCMab1 treatment downregulated phosphorylation of FAK and c-Jun, reduced expression level of cyclin D1 and CDK4, and interfered with cell proliferation and cell cycles. Therefore, aberrantly glycosylated integrin α3β1 might result in malignant transformation of cells. BCMab1 could suppress tumor growth by inhibiting angiogenesis in the microenvironment of bladder cancer tumor. BCMab1 downregulated the generation of VEGF and IL-6 in tumors, which suggested that targeting of tumor microenvironment required further investigation.

EXAMPLE 11

Consistency Between Aberrant Glycosylation Level of Integrin α3β1 and the Severity Degree and Lifetime of Cancer Patients In order to determine whether the aberrant glycosylation expression level of integrin α3β1 is consistent with the clinical manifestation of cancer patients, immunohistochemical assays were conducted to the patients suffering from bladder cancer. The bladder cancer tissues obtained from 69 patients in Grades 1-3 (G1-3) and Stages 1-4 (T1-4) were detected. Weak staining occurred in the patients with low grades (G1-G2) and low stages (T1-T2) (FIG. 17, a and Table 5); whereas intense BCMab1 staining occurred in the patients with a high grade and high stages (G3 and T3, T4). The staining of normal bladder tissue was used as a control. As a result, the aberrant glycosylation expression level of integrin α3β1 was consistent with the severity degrees of cancer patients.

Figure 17:
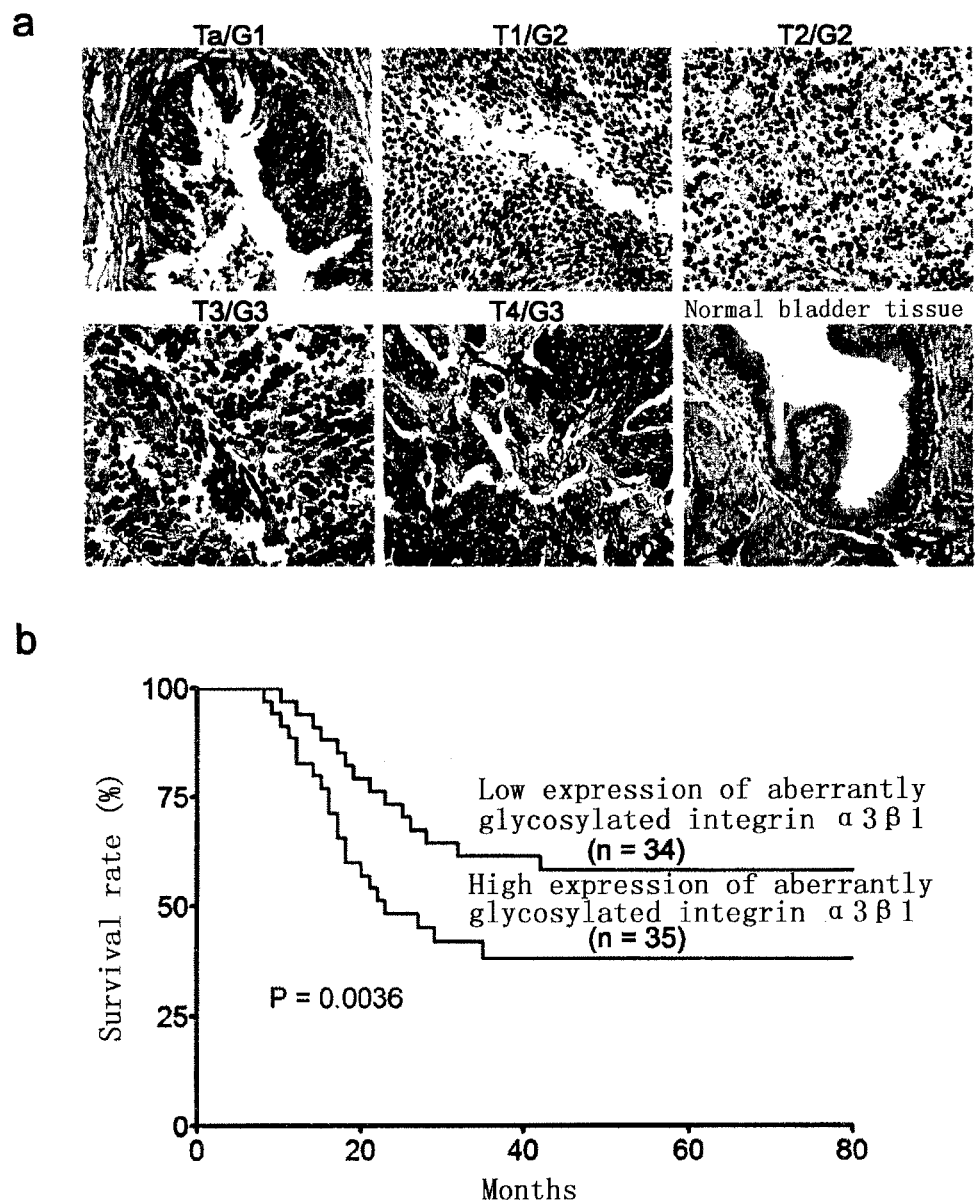
FIG. 17. Aberrant glycosylation of integrin α3β1 was correlated with clinical severity and prognosis. (a) Immunohistochemical results showed that aberrant glycosylation expression level of integrin α3β1 was correlated with clinical characters. The intensity of BCMab1 staining was related with pathological staging and grading. (b) According to the visits for the prognoses of bladder cancer patients in combination with immunohistochemical analysis, it was indicated that expression of integrin α3β1 was correlated with pathological characters in clinic. The expression level of integrin α3β1 was high in the bladder cancer specimen with a higher grade, deeper invasion and lymph-node involvement; whereas low in the case with a lower grade, superficial invasion and lymph-node involvement-free. The patients with high expression levels of integrin α3β1 showed poor prognoses (p=0.0036).

We also analyzed the aberrant glycosylation expression of integrin α3β1 and clinical pathological features in the patients who had experienced radical cystectomy. The aberrant glycosylation expression of integrin α3β1 was higher in the bladder cancer patients with high stages, deep invasion and lymph-node involvement than in the patients with low grades, shallow invasion and no lymph-node involvement (Table 5). The patients with a higher aberrant glycosylation expression of integrin α3β1 had a lower survival rate than the patients with lower expression (P>0.0036) (FIG. 17, b).

TABLE 5

Integrin α3β1 modified by abnormal glycosylation is intimately correlated with clinical pathology of bladder cancer tissues

| Total | | Patients | Expression of aberrantly glycosylated Integrin α3β1 | | |
|---|---|---|---|---|---|
| | | | High | Low | P |
| Age | Mean | 62.3 | 65.7 | 58.9 | 0.352 |
| Sex | Male | 48 | 25 | 23 | 0.732 |
| | Female | 21 | 10 | 11 | |
| Tumor stage | Ta, Tis, T1 | 26 | 5 | 21 | <0.001 |
| | T2 | 15 | 9 | 6 | |
| | T3 | 20 | 13 | 7 | |
| | T4 | 8 | 5 | 3 | |
| Grade | G1 or 2 | 22 | 5 | 17 | <0.001 |
| | G3 | 47 | 32 | 15 | |
| Configuration | Papillary | 17 | 6 | 11 | 0.108 |
| | Nonpapillary | 52 | 30 | 22 | |
| Number of tumors | Solitary | 38 | 23 | 15 | 0.071 |
| | Multiple | 31 | 12 | 19 | |
| Lymphatic invasion | Negative | 18 | 2 | 16 | <0.005 |
| | Positive | 39 | 21 | 18 | |
| | Unknown | 12 | 7 | 5 | |
| Follow-up (month) | Mean | 72.6 | 70.3 | 74.9 | 0.478 |

Bladder cancer is a common disease with an incidence increasing year after year. More and more evidence demonstrated that molecular signal pathway affected cell stability and thus caused bladder cancer. Cell growth mainly involves five aspects, including cell cycle, cell death, cell growth, signal transduction, and gene regulation. Both the influence of external carcinogenic signals or variation of genetic factors may result in signal disorder. Maintenance and progress of tumors depend on two external factors, i.e. the correlations between interstitial substance and knizocyte, and between angiogenesis and tumor cell invasion. However, the molecular mechanism for malignant transformation of bladder cancer was still unknown. The novel monoclonal antibody BCMab1 prepared by the inventors could specifically bind to aberrantly glycosylated integrin α3β1 and recognize aberrantly glycosylated α3 subunit. High expression of glycosyltransferase GALNT1 may result in aberrant glycosylation of integrin α3. Knockdown of integrin α3 or GALNT1 could inhibit proliferation of cancers and growth of tumors in vivo and in vitro. As such, block of integrin α3 signal by BCMab1 could also inhibit proliferation of cancers and growth of tumors. In addition, aberrant glycosylation level of integrin α3β1 was correlated with clinical staging and prognosis of bladder cancer. The results suggested that aberrant glycosylation of integrin α3β1 was correlated with occurrence of bladder cancer. Aberrant glycosylation of integrin α3β1 could become a new diagnosis marker for bladder cancer and a new indicator for prognosis.

EXAMPLE 12

Preparation of Immunodiagnosis Reagent for Bladder Cancer

Using the antigen AG-α3β1 and antibody BCMab1 described in the invention, a hypersensitized competitive ELISA method is developed in the invention to detect bladder tumors in human urine. The major process includes steps of using antigen AG-α3β1 as an immobile phase and standard sample; using antibody BCMab1 as a detection antibody in combination with the secondary antibody (horseradish peroxidase (HRP) labeled goat-anti-mouse IgG); and detecting bladder cancer antigen AG-α3β1 in urine of normal human and bladder cancer patients. It was proved by the experiments that the immunodiagnosis reagent for bladder cancer according to the invention had, compared with prior art, the following positive effects: (1) it directly detects urine liquid without injury, so as to avoid inconvenience and distress caused to patients by cystoscopy; (2) it has a high sensitivity and specificity that are much higher than those of the detection of current bladder tumor marker (such as nuclear matrix protein, cytokeratin, hyaluronic acid and the like) and pathological examination of urine exfoliative cells; (3) it has a high specificity and sensitivity and utilizes competitive ELISA to detect bladder cancer antigen in cells, so as to avoid the defects of higher factitiousness and lower sensitivity which cannot be overcome by cell pathology itself; and (4) it is convenient and fast, thereby suitable for screening early-stage bladder cancer patients and detecting relapse of tumors.

Detailed experiment procedure is shown as follows:
1) Sample source and clinical data: urine of healthy volunteers and bladder cancer patients were obtained from Peking University Third Hospital.
2) Detailed steps:
  i) coating ELISA plate with antigen: antigen AG-α3β1 was diluted to 1 μg/mL with PBS and coated on a plate, 50 μg/well, at 4° C. overnight.
  ii) blocking nonspecific binding sites: incubated with 2% BSA/PBS, 200 μg/well, at 37° C. for 2 hours.
  iii) incubating samples: the samples to be tested were fresh urine; the loading amount was 50 μL; urine obtained from healthy volunteers was used as the negative control; 1 μg/mL antibody BCMab1 (50 μL) was added to each well; each sample was duplicated and incubated at 37° C. for 1 hour.
  iv) washing with PBST for 5 times.
  v) adding horseradish peroxidase (HRP) labeled goat-anti-mouse IgG antibody (Sigma Co.), 100 μL/well, incubating at 37° C. for 1 hour.
  vi) washing with PBST for 5 times.
  vii) adding substrate (tetramethyl benzidine, $H_2O_2$), 100 μL/well, incubating in dark at room temperature for 10-20 min; adding 2M $H_2SO_4$ (50 μL) to terminate the reaction; measuring OD (450 nm) value by an Microplate reader.
2) Result analysis: according to negative OD value/OD critical value≈2.1, OD critical value≈negative OD value/2.1; then the sensitivity and specificity could be determined in accordance with OD critical value.

|  |  | Actual Samples | | |
| --- | --- | --- | --- | --- |
|  |  | + | − | Total |
| Detection Results | + | 82 | 7 | 89 |
|  | − | 18 | 93 | 111 |
| Total |  | 100 | 100 | 200 |

Clinical sensitivity can be used to evaluate the capability of a certain assay to detect sick subjects, and sensitivity is the proportion of true positives correctly identified in the actual sick subjects.

In the experiment, sensitivity=82/(82+18)×%=82%.

Clinical specificity can be used to evaluate the capability of a certain assay to identify healthy subjects, and specificity is the proportion of true negatives correctly identified in the actual healthy subjects.

In the experiment, specificity=93/(7+93)×%=93%.

EXAMPLE 13

Screening for Potential Medicaments to Treat Bladder Cancer

T24 cells, endogenously expressing GAL3ST2 protein, were taken and cultured as above. The cells were used as cell models to screen for the medicaments to treat bladder cancer in mammals.

Test group: the above cell culture was treated with a candidate;

Control group: the above cell culture was not treated with the candidate.

After treated for a proper time period, the cells were detected for GAL3ST2 expression, enzyme activities, existing amount or secretion status by conventional methods. Compared with the control group, GAL3ST2 protein expression, enzyme activities, existing amount or secretion was significantly reduced by 30% or more in the test group, which indicated that such a candidate is a potential substance to treat bladder cancer.

Confirmation: RNAi sequence of GAL3ST2 was tested as a candidate. The result showed that GAL3ST2 protein expression was inhibited. Thus the RNAi sequence is a potential substance to treat bladder cancer.

EXAMPLE 14

Screening for Potential Medicaments to Treat Bladder Cancer

T24 cells, endogenously expressing N-acetylgalactosaminyltransferase 1 protein, were taken and cultured as above. The cells were used as cell models to screen for the medicaments to treat bladder cancer in mammals.

Test group: the above cell culture was treated with a candidate;

Control group: the above cell culture was not treated with the candidate.

After treated for a proper time period, the cells were detected for N-acetylgalactosaminyltransferase 1 expression, enzyme activities, existing amount or secretion status by conventional methods. Compared with the control group, N-acetylgalactosaminyltransferase 1 protein expression, enzyme activities, existing amount or secretion was significantly reduced by 30% or more in the test group, which indicated that such a candidate is a potential substance to treat bladder cancer.

Confirmation: RNAi sequence of N-acetylgalactosaminyltransferase 1 was tested as a candidate. The result showed that N-acetylgalactosaminyltransferase 1 protein expression was inhibited. Thus the RNAi sequence is a potential substance to treat bladder cancer.

Although the detailed Examples of the invention are illustrated as above, it can be understood that the invention can be conducted in a practice other than the above illustrations, and the protection scope of the invention is not limited by the description.

The invention claimed is:

1. A binding molecule directed agains an aberrantly glycosylated integrin AG-α3β1,
wherein the AG-α3β1 comprises a carbohydrate [3OSO3] Galβ1-4(Fucα1-3)[6OSO3]GlcNAc as an antigenic epitope having a structure of:

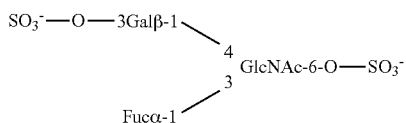

wherein the binding molecule recognises or binds to the carbohydrate and is an anti-AG-α3β1 monoclonal antibody BCMab1 secreted by a hydridoma call line deposited as CGMCC No. 3845.

2. The binding molecule according to claim 1, wherein the binding molecule is conjugated with a radioactive agent.

3. The binding molecule according to claim 1, wherein the binding molecule is composition that comprises the binding molecule and a pharmaceutically acceptable carrier, diluents or excipient, and wherein the binding molecule is a radioactive agent.

4. A kit for detecting bladder cancer, comprising a binding molecule directed against an aberrantly glycosylated intergrin AG-α3β1; and optionally another reagent for detecting bladder cancer,
wherein the binding molecule is optionally conjugated with a substance selected from the group consisting of a biological marker, an antitumor drug, a toxin, and a radioactive agent,
wherein the AG-α3β1 comprises a carbohydrate [3OSO3] Galβ1-4(Fucα1-3)[6OSO3]GlcNAc as an antigenic epitope having a structure of:

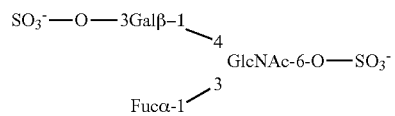

wherein the binding molecule recongnizes or binds to the carbohydrate and is an anti-AG-α3β1 monoclonal antibody BCMab1 secreted by a hybridoma cell line deposited as CGMCC No. 3845.

5. The kit according to claim 4, wherein the detection is carried out by an enzyme linked immunosorbent assay.

6. The kit according to claim 4, wherein the sample to be tested is urine or bladder tissue.

7. A hybridoma cell line secreting antibody BCMab1 directed against integrin α3β1 of human bladder cancer, wherein the hybridoma cell line is deposited as CGMCC No. 3845.

8. A method for diagnosing bladder with the anti-AG-α3β1 monoclonal antibody BCMab1 according to claim 1, the method comprising:
   contacting the antibody with a test sample obtained for a subject,
   dertermining an amount of antigen-antibody binding, and
   determining the subject having bladder cancer if an antigen-antibody binding is present.

* * * * *

SEQUENCE LISTING

<160> NUMBER OF SEQ ID NOS: 41

<210> SEQ ID NO 1
<211> LENGTH: 1051
<212> TYPE: PRT
<213> ORGANISM: Homo sapiens

<400> SEQUENCE: 1

```
Met Gly Pro Gly Pro Ser Arg Ala Pro Arg Ala Pro Arg Leu Met Leu
1               5                   10                  15

Cys Ala Leu Ala Leu Met Val Ala Ala Gly Gly Cys Val Val Ser Ala
                20                  25                  30

Phe Asn Leu Asp Thr Arg Phe Leu Val Val Lys Glu Ala Gly Asn Pro
                35                  40                  45

Gly Ser Leu Phe Gly Tyr Ser Val Ala Leu His Arg Gln Thr Glu Arg
            50                  55                  60

Gln Gln Arg Tyr Leu Leu Leu Ala Gly Ala Pro Arg Glu Leu Ala Val
65                  70                  75                  80

Pro Asp Gly Tyr Thr Asn Arg Thr Gly Ala Val Tyr Leu Cys Pro Leu
                85                  90                  95

Thr Ala His Lys Asp Asp Cys Glu Arg Met Asn Ile Thr Val Lys Asn
                100                 105                 110

Asp Pro Gly His His Ile Ile Glu Asp Met Trp Leu Gly Val Thr Val
                115                 120                 125

Ala Ser Gln Gly Pro Ala Gly Arg Val Leu Val Cys Ala His Arg Tyr
            130                 135                 140

Thr Gln Val Leu Trp Ser Gly Ser Glu Asp Gln Arg Arg Met Val Gly
145                 150                 155                 160

Lys Cys Tyr Val Arg Gly Asn Asp Leu Glu Leu Asp Ser Ser Asp Asp
                165                 170                 175

Trp Gln Thr Tyr His Asn Glu Met Cys Asn Ser Asn Thr Asp Tyr Leu
                180                 185                 190

Glu Thr Gly Met Cys Gln Leu Gly Thr Ser Gly Gly Phe Thr Gln Asn
                195                 200                 205

Thr Val Tyr Phe Gly Ala Pro Gly Ala Tyr Asn Trp Lys Gly Asn Ser
            210                 215                 220

Tyr Met Ile Gln Arg Lys Glu Trp Asp Leu Ser Glu Tyr Ser Tyr Lys
225                 230                 235                 240

Asp Pro Glu Asp Gln Gly Asn Leu Tyr Ile Gly Tyr Thr Met Gln Val
                245                 250                 255

Gly Ser Phe Ile Leu His Pro Lys Asn Ile Thr Ile Val Thr Gly Ala
            260                 265                 270

Pro Arg His Arg His Met Gly Ala Val Phe Leu Leu Ser Gln Glu Ala
                275                 280                 285

Gly Gly Asp Leu Arg Arg Arg Gln Val Leu Glu Gly Ser Gln Val Gly
            290                 295                 300

Ala Tyr Phe Gly Ser Ala Ile Ala Leu Ala Asp Leu Asn Asn Asp Gly
305                 310                 315                 320

Trp Gln Asp Leu Leu Val Gly Ala Pro Tyr Tyr Phe Glu Arg Lys Glu
                325                 330                 335

Glu Val Gly Gly Ala Ile Tyr Val Phe Met Asn Gln Ala Gly Thr Ser
                340                 345                 350

Phe Pro Ala His Pro Ser Leu Leu Leu His Gly Pro Ser Gly Ser Ala
            355                 360                 365
```

```
Phe Gly Leu Ser Val Ala Ser Ile Gly Asp Ile Asn Gln Asp Gly Phe
    370                 375                 380

Gln Asp Ile Ala Val Gly Ala Pro Phe Glu Gly Leu Gly Lys Val Tyr
385                 390                 395                 400

Ile Tyr His Ser Ser Lys Gly Leu Leu Arg Gln Pro Gln Gln Val
                405                 410                 415

Ile His Gly Glu Lys Leu Gly Leu Pro Gly Leu Ala Thr Phe Gly Tyr
            420                 425                 430

Ser Leu Ser Gly Gln Met Asp Val Asp Glu Asn Phe Tyr Pro Asp Leu
        435                 440                 445

Leu Val Gly Ser Leu Ser Asp His Ile Val Leu Arg Ala Arg Pro
    450                 455                 460

Val Ile Asn Ile Val His Lys Thr Leu Val Pro Arg Pro Ala Val Leu
465                 470                 475                 480

Asp Pro Ala Leu Cys Thr Ala Thr Ser Cys Val Gln Val Glu Leu Cys
                485                 490                 495

Phe Ala Tyr Asn Gln Ser Ala Gly Asn Pro Asn Tyr Arg Arg Asn Ile
            500                 505                 510

Thr Leu Ala Tyr Thr Leu Glu Ala Asp Arg Asp Arg Arg Pro Pro Arg
        515                 520                 525

Leu Arg Phe Ala Gly Ser Glu Ser Ala Val Phe His Gly Phe Phe Ser
    530                 535                 540

Met Pro Glu Met Arg Cys Gln Lys Leu Glu Leu Leu Met Asp Asn
545                 550                 555                 560

Leu Arg Asp Lys Leu Arg Pro Ile Ile Ile Ser Met Asn Tyr Ser Leu
                565                 570                 575

Pro Leu Arg Met Pro Asp Arg Pro Arg Leu Gly Leu Arg Ser Leu Asp
            580                 585                 590

Ala Tyr Pro Ile Leu Asn Gln Ala Gln Ala Leu Glu Asn His Thr Glu
        595                 600                 605

Val Gln Phe Gln Lys Glu Cys Gly Pro Asp Asn Lys Cys Glu Ser Asn
    610                 615                 620

Leu Gln Met Arg Ala Ala Phe Val Ser Glu Gln Gln Gln Lys Leu Ser
625                 630                 635                 640

Arg Leu Gln Tyr Ser Arg Asp Val Arg Lys Leu Leu Leu Ser Ile Asn
                645                 650                 655

Val Thr Asn Thr Arg Thr Ser Glu Arg Ser Gly Glu Asp Ala His Glu
            660                 665                 670

Ala Leu Leu Thr Leu Val Val Pro Pro Ala Leu Leu Leu Ser Ser Val
        675                 680                 685

Arg Pro Pro Gly Ala Cys Gln Ala Asn Glu Thr Ile Phe Cys Glu Leu
    690                 695                 700

Gly Asn Pro Phe Lys Arg Asn Gln Arg Met Glu Leu Leu Ile Ala Phe
705                 710                 715                 720

Glu Val Ile Gly Val Thr Leu His Thr Arg Asp Leu Gln Val Gln Leu
                725                 730                 735

Gln Leu Ser Thr Ser Ser His Gln Asp Asn Leu Trp Pro Met Ile Leu
            740                 745                 750

Thr Leu Leu Val Asp Tyr Thr Leu Gln Thr Ser Leu Ser Met Val Asn
        755                 760                 765

His Arg Leu Gln Ser Phe Phe Gly Gly Thr Val Met Gly Glu Ser Gly
    770                 775                 780

Met Lys Thr Val Glu Asp Val Gly Ser Pro Leu Lys Tyr Glu Phe Gln
```

```
Val Gly Pro Met Gly Glu Gly Leu Val Gly Leu Gly Thr Leu Val Leu
        785                 790                 795                 800
Gly Leu Glu Trp Pro Tyr Glu Val Ser Asn Gly Lys Trp Leu Leu Tyr
            805                 810                 815
Pro Thr Glu Ile Thr Val His Gly Asn Gly Ser Trp Pro Cys Arg Pro
            820                 825                 830
Pro Gly Asp Leu Ile Asn Pro Leu Asn Leu Thr Leu Ser Asp Pro Gly
835                 840                 845
Asp Arg Pro Ser Ser Pro Gln Arg Arg Arg Gln Leu Asp Pro Gly
850                 855                 860
Gly Gly Gln Gly Pro Pro Val Thr Leu Ala Ala Lys Lys Ala
865                 870                 875                 880
Lys Ser Glu Thr Val Leu Thr Cys Ala Thr Gly Arg Ala His Cys Val
            885                 890                 895
Trp Leu Glu Cys Pro Ile Pro Asp Ala Pro Val Val Thr Asn Val Thr
            900                 905                 910
Val Lys Ala Arg Val Trp Asn Ser Thr Phe Ile Glu Asp Tyr Arg Asp
            915                 920                 925
Phe Asp Arg Val Arg Val Asn Gly Trp Ala Thr Leu Phe Leu Arg Thr
945                 950                 955                 960
Ser Ile Pro Thr Ile Asn Met Glu Asn Lys Thr Thr Trp Phe Ser Val
            965                 970                 975
Asp Ile Asp Ser Glu Leu Val Glu Glu Leu Pro Ala Glu Ile Glu Leu
            980                 985                 990
Trp Leu Val Leu Val Ala Val Gly Ala Gly Leu Leu Leu Leu Gly Leu
            995                 1000                1005
Ile Ile Leu Leu Leu Trp Lys Cys Gly Phe Phe Lys Arg Ala Arg
            1010                1015                1020
Thr Arg Ala Leu Tyr Glu Ala Lys Arg Gln Lys Ala Glu Met Lys
            1025                1030                1035
Ser Gln Pro Ser Glu Thr Glu Arg Leu Thr Asp Asp Tyr
            1040                1045                1050

<210> SEQ ID NO 2
<211> LENGTH: 798
<212> TYPE: PRT
<213> ORGANISM: Homo sapiens

<400> SEQUENCE: 2

Met Asn Leu Gln Pro Ile Phe Trp Ile Gly Leu Ile Ser Ser Val Cys
1               5                   10                  15
Cys Val Phe Ala Gln Thr Asp Glu Asn Arg Cys Leu Lys Ala Asn Ala
                20                  25                  30
Lys Ser Cys Gly Glu Cys Ile Gln Ala Gly Pro Asn Cys Gly Trp Cys
            35                  40                  45
Thr Asn Ser Thr Phe Leu Gln Glu Gly Met Pro Thr Ser Ala Arg Cys
        50                  55                  60
Asp Asp Leu Glu Ala Leu Lys Lys Lys Gly Cys Pro Pro Asp Asp Ile
65                  70                  75                  80
Glu Asn Pro Arg Gly Ser Lys Asp Ile Lys Lys Asn Lys Asn Val Thr
                85                  90                  95
Asn Arg Ser Lys Gly Thr Ala Glu Lys Leu Lys Pro Glu Asp Ile Thr
            100                 105                 110
```

-continued

```
Gln Ile Gln Pro Gln Gln Leu Val Leu Arg Leu Arg Ser Gly Glu Pro
            115                 120                 125

Gln Thr Phe Thr Leu Lys Phe Lys Arg Ala Glu Asp Tyr Pro Ile Asp
        130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
        290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
        355                 360                 365

Gln Leu Ile Ile Asp Ala Tyr Asn Ser Leu Ser Ser Glu Val Ile Leu
    370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
            420                 425                 430

Asn Lys Cys Pro Lys Lys Asp Ser Asp Ser Phe Lys Ile Arg Pro Leu
        435                 440                 445

Gly Phe Thr Glu Glu Val Glu Val Ile Leu Gln Tyr Ile Cys Glu Cys
    450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
            500                 505                 510

Asp Ala Tyr Cys Arg Lys Glu Asn Ser Ser Glu Ile Cys Ser Asn Asn
        515                 520                 525

Gly Glu Cys Val Cys Gly Gln Cys Val Cys Arg Lys Arg Asp Asn Thr
```

```
                        530                 535                 540
Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
            580                 585                 590

Ser Leu Asp Thr Ser Thr Cys Glu Ala Ser Asn Gly Gln Ile Cys Asn
        595                 600                 605

Gly Arg Gly Ile Cys Glu Cys Gly Val Cys Lys Cys Thr Asp Pro Lys
    610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
        675                 680                 685

Ser His Cys Lys Glu Lys Asp Val Asp Asp Cys Trp Phe Tyr Phe Thr
    690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
cggtcaccaa catcatgtt                                           19

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
ccagtacaaa agcctcatg                                           19

<210> SEQ ID NO 5
<211> LENGTH: 15
<212> TYPE: PRT
<213> ORGANISM: Homo sapiens
```

<400> SEQUENCE: 5

Arg Thr Gly Ala Val Tyr Leu Cys Pro Leu Thr Ala His Lys Asp
1               5                   10                  15

<210> SEQ ID NO 6
<211> LENGTH: 15
<212> TYPE: PRT
<213> ORGANISM: Homo sapiens

<400> SEQUENCE: 6

Arg Tyr Thr Gln Val Leu Trp Ser Gly Ser Glu Asp Gln Arg Arg
1               5                   10                  15

<210> SEQ ID NO 7
<211> LENGTH: 11
<212> TYPE: PRT
<213> ORGANISM: Homo sapiens

<400> SEQUENCE: 7

Arg Tyr Leu Leu Leu Ala Gly Ala Pro Arg Glu
1               5                   10

<210> SEQ ID NO 8
<211> LENGTH: 18
<212> TYPE: PRT
<213> ORGANISM: Homo sapiens

<400> SEQUENCE: 8

Arg Leu Gln Ser Phe Phe Gly Gly Thr Val Met Gly Glu Ser Gly Met
1               5                   10                  15

Lys Thr

<210> SEQ ID NO 9
<211> LENGTH: 19
<212> TYPE: PRT
<213> ORGANISM: Homo sapiens

<400> SEQUENCE: 9

Lys Glu Ala Gly Asn Pro Gly Ser Leu Phe Gly Tyr Ser Val Ala Leu
1               5                   10                  15

His Arg Gln

<210> SEQ ID NO 10
<211> LENGTH: 19
<212> TYPE: PRT
<213> ORGANISM: Homo sapiens

<400> SEQUENCE: 10

Arg His Met Gly Ala Val Phe Leu Leu Ser Gln Glu Ala Gly Gly Asp
1               5                   10                  15

Leu Arg Arg

<210> SEQ ID NO 11
<211> LENGTH: 18
<212> TYPE: PRT
<213> ORGANISM: Homo sapiens

<400> SEQUENCE: 11

Arg Leu Gly Ser Phe Phe Gly Gly Thr Val Met Gly Glu Ser Gly Met
1               5                   10                  15

Lys Thr

<210> SEQ ID NO 12
<211> LENGTH: 12
<212> TYPE: PRT
<213> ORGANISM: Homo sapiens

<400> SEQUENCE: 12

Lys Leu Glu Leu Leu Leu Met Asp Asn Leu Arg Asp
1               5                   10

<210> SEQ ID NO 13
<211> LENGTH: 21
<212> TYPE: PRT
<213> ORGANISM: Homo sapiens

<400> SEQUENCE: 13

Arg Phe Ala Gly Ser Glu Ser Ala Val Phe His Gly Phe Phe Ser Met
1               5                   10                  15

Pro Glu Met Arg Cys
            20

<210> SEQ ID NO 14
<211> LENGTH: 18
<212> TYPE: PRT
<213> ORGANISM: Homo sapiens

<400> SEQUENCE: 14

Arg Leu Gln Ser Phe Phe Gly Gly Thr Val Met Gly Glu Ser Gly Met
1               5                   10                  15

Lys Thr

<210> SEQ ID NO 15
<211> LENGTH: 12
<212> TYPE: PRT
<213> ORGANISM: Homo sapiens

<400> SEQUENCE: 15

Lys Ser Ala Val Thr Thr Val Val Asn Pro Lys Tyr
1               5                   10

<210> SEQ ID NO 16
<211> LENGTH: 15
<212> TYPE: PRT
<213> ORGANISM: Homo sapiens

<400> SEQUENCE: 16

Arg Ser Asn Gly Leu Ile Cys Gly Gly Asn Gly Val Cys Lys Cys
1               5                   10                  15

<210> SEQ ID NO 17
<211> LENGTH: 18
<212> TYPE: PRT
<213> ORGANISM: Homo sapiens

<400> SEQUENCE: 17

Arg Asp Lys Leu Pro Gln Pro Val Gln Pro Asp Pro Val Ser His Cys
1               5                   10                  15

Lys Glu

<210> SEQ ID NO 18
<211> LENGTH: 13
<212> TYPE: PRT
<213> ORGANISM: Homo sapiens

<400> SEQUENCE: 18

Lys Phe Cys Glu Cys Asp Asn Phe Asn Cys Asp Arg Ser
1               5                   10

<210> SEQ ID NO 19
<211> LENGTH: 12
<212> TYPE: PRT
<213> ORGANISM: Homo sapiens

<400> SEQUENCE: 19

Lys Leu Ser Glu Gly Val Thr Ile Ser Tyr Lys Ser
1               5                   10

<210> SEQ ID NO 20
<211> LENGTH: 12
<212> TYPE: PRT
<213> ORGANISM: Homo sapiens

<400> SEQUENCE: 20

Lys Trp Asp Thr Gly Glu Asn Pro Ile Tyr Lys Ser
1               5                   10

<210> SEQ ID NO 21
<211> LENGTH: 11
<212> TYPE: PRT
<213> ORGANISM: Homo sapiens

<400> SEQUENCE: 21

Arg Ile Gly Phe Gly Ser Phe Val Glu Lys Thr
1               5                   10

<210> SEQ ID NO 22
<211> LENGTH: 13
<212> TYPE: PRT
<213> ORGANISM: Homo sapiens

<400> SEQUENCE: 22

Lys Ser Leu Gly Thr Asp Leu Met Asn Glu Met Arg Arg
1               5                   10

<210> SEQ ID NO 23
<211> LENGTH: 19
<212> TYPE: PRT
<213> ORGANISM: Homo sapiens

<400> SEQUENCE: 23

Lys Leu Lys Pro Glu Asp Ile Thr Gln Ile Gln Pro Gln Gln Leu Val
1               5                   10                  15

Leu Arg Leu

<210> SEQ ID NO 24
<211> LENGTH: 20
<212> TYPE: PRT
<213> ORGANISM: Homo sapiens

<400> SEQUENCE: 24

Lys Asn Val Leu Ser Leu Thr Asn Lys Gly Glu Val Phe Asn Glu Leu
1               5                   10                  15

Val Gly Lys Gln
            20

<210> SEQ ID NO 25

```
<211> LENGTH: 19
<212> TYPE: PRT
<213> ORGANISM: Homo sapiens

<400> SEQUENCE: 25

Arg Leu Leu Val Phe Ser Thr Asp Ala Gly Phe His Phe Ala Gly Asp
1               5                   10                  15

Gly Lys Leu

<210> SEQ ID NO 26
<211> LENGTH: 23
<212> TYPE: PRT
<213> ORGANISM: Homo sapiens

<400> SEQUENCE: 26

Lys Leu Ser Glu Asn Asn Ile Gln Thr Ile Phe Ala Val Thr Glu Glu
1               5                   10                  15

Phe Gln Pro Val Tyr Lys Glu
            20

<210> SEQ ID NO 27
<211> LENGTH: 21
<212> TYPE: PRT
<213> ORGANISM: Homo sapiens

<400> SEQUENCE: 27

Arg Ala Glu Asp Tyr Pro Ile Asp Leu Tyr Tyr Leu Met Asp Leu Ser
1               5                   10                  15

Tyr Ser Met Lys Asp
            20

<210> SEQ ID NO 28
<211> LENGTH: 60
<212> TYPE: DNA
<213> ORGANISM: Artificial Sequence
<220> FEATURE:
<223> OTHER INFORMATION: Synthetic

<400> SEQUENCE: 28
gatccccgct acatgattca gcgcaattca agagattgcg ctgaatcatg tagcttttta    60

<210> SEQ ID NO 29
<211> LENGTH: 60
<212> TYPE: DNA
<213> ORGANISM: Artificial Sequence
<220> FEATURE:
<223> OTHER INFORMATION: Synthetic

<400> SEQUENCE: 29
agcttaaaaa gctacatgat tcagcgcaat ctcttgaatt gcgctgaatc atgtagcggg    60

<210> SEQ ID NO 30
<211> LENGTH: 60
<212> TYPE: DNA
<213> ORGANISM: Artificial Sequence
<220> FEATURE:
<223> OTHER INFORMATION: Synthetic

<400> SEQUENCE: 30
gatccccgct gaagactatc ccattgttca agagacaatg ggatagtctt cagcttttta    60

<210> SEQ ID NO 31
<211> LENGTH: 60
<212> TYPE: DNA
```

```
<213> ORGANISM: Artificial Sequence
<220> FEATURE:
<223> OTHER INFORMATION: Synthetic

<400> SEQUENCE: 31
agcttaaaaa gctgaagact atcccattgt ctcttgaaca atgggatagt cttcagcggg    60

<210> SEQ ID NO 32
<211> LENGTH: 60
<212> TYPE: DNA
<213> ORGANISM: Artificial Sequence
<220> FEATURE:
<223> OTHER INFORMATION: Synthetic

<400> SEQUENCE: 32
gatcccccgg tcaccaacat catgttttca agagaaacat gatgttggtg accgttttta    60

<210> SEQ ID NO 33
<211> LENGTH: 60
<212> TYPE: DNA
<213> ORGANISM: Artificial Sequence
<220> FEATURE:
<223> OTHER INFORMATION: Synthetic

<400> SEQUENCE: 33
agcttaaaaa cggtcaccaa catcatgttt ctcttgaaaa catgatgttg gtgaccgggg    60

<210> SEQ ID NO 34
<211> LENGTH: 60
<212> TYPE: DNA
<213> ORGANISM: Artificial Sequence
<220> FEATURE:
<223> OTHER INFORMATION: Synthetic

<400> SEQUENCE: 34 gatccccctcc gaaacctgct cttcttttca agagaaagaa gagcaggttt cggattttta    60

<210> SEQ ID NO 35
<211> LENGTH: 60
<212> TYPE: DNA
<213> ORGANISM: Artificial Sequence
<220> FEATURE:
<223> OTHER INFORMATION: Synthetic

<400> SEQUENCE: 35
agcttaaaaa tccgaaacct gctcttcttt ctcttgaaaa gaagagcagg tttcggaggg    60

<210> SEQ ID NO 36
<211> LENGTH: 60
<212> TYPE: DNA
<213> ORGANISM: Artificial Sequence
<220> FEATURE:
<223> OTHER INFORMATION: Synthetic

<400> SEQUENCE: 36
gatccccggt gcagaacatc ctgttttca agagaaaaca ggatgttctg caccttttta    60

<210> SEQ ID NO 37
<211> LENGTH: 60
<212> TYPE: DNA
<213> ORGANISM: Artificial Sequence
<220> FEATURE:
<223> OTHER INFORMATION: Synthetic

<400> SEQUENCE: 37
agcttaaaaa ggtgcagaac atcctgtttt ctcttgaaaa acaggatgtt ctgcaccggg    60
```

```
<210> SEQ ID NO 38
<211> LENGTH: 60
<212> TYPE: DNA
<213> ORGANISM: Artificial Sequence
<220> FEATURE:
<223> OTHER INFORMATION: Synthetic

<400> SEQUENCE: 38 gatcccggt gcagaacatc ctgtttttca agagaaaaca ggatgttctg caccttttta        60

<210> SEQ ID NO 39
<211> LENGTH: 60
<212> TYPE: DNA
<213> ORGANISM: Artificial Sequence
<220> FEATURE:
<223> OTHER INFORMATION: Synthetic

<400> SEQUENCE: 39
agcttaaaaa tccgcaagtc accatctttt ctcttgaaaa agatggtgac ttgcggaggg        60

<210> SEQ ID NO 40
<211> LENGTH: 60
<212> TYPE: DNA
<213> ORGANISM: Artificial Sequence
<220> FEATURE:
<223> OTHER INFORMATION: Synthetic

<400> SEQUENCE: 40 gatccccca gtacaaaagc ctcatgttca agagacatga ggcttttgta ctggttttta        60

<210> SEQ ID NO 41
<211> LENGTH: 60
<212> TYPE: DNA
<213> ORGANISM: Artificial Sequence
<220> FEATURE:
<223> OTHER INFORMATION: Synthetic

<400> SEQUENCE: 41
agcttaaaaa ccagtacaaa agcctcatgt ctcttgaaca tgaggctttt gtactggggg        60
```